(12) United States Patent
Prestrelski et al.

(10) Patent No.: US 9,295,724 B2
(45) Date of Patent: *Mar. 29, 2016

(54) STABLE FORMULATIONS FOR PARENTERAL INJECTION OF PEPTIDE DRUGS

(71) Applicant: Xeris Pharmaceuticals, Inc., Austin, TX (US)

(72) Inventors: Steven Prestrelski, San Diego, CA (US); John Kinzell, San Rafael, CA (US)

(73) Assignee: Xeris Pharmaceuticals, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,679

(22) Filed: Feb. 27, 2014

(65) Prior Publication Data

US 2014/0179599 A1 Jun. 26, 2014

Related U.S. Application Data

(62) Division of application No. 13/417,073, filed on Mar. 9, 2012, now Pat. No. 8,697,644.

(60) Provisional application No. 61/609,123, filed on Mar. 9, 2012, provisional application No. 61/553,388, filed on Oct. 31, 2011, provisional application No. 61/478,692, filed on Apr. 25, 2011, provisional application No. 61/451,568, filed on Mar. 10, 2011.

(51) Int. Cl.

| | | |
|---|---|---|
| *A61K 47/22* | (2006.01) | |
| *A61K 47/20* | (2006.01) | |
| *A61K 38/26* | (2006.01) | |
| *A61K 47/26* | (2006.01) | |
| *A61K 9/00* | (2006.01) | |
| *A61K 9/19* | (2006.01) | |
| *A61K 38/22* | (2006.01) | |
| *A61K 38/28* | (2006.01) | |
| *A61K 47/02* | (2006.01) | |
| *A61K 47/10* | (2006.01) | |
| *A61K 47/12* | (2006.01) | |
| *A61K 47/14* | (2006.01) | |
| *A61K 47/18* | (2006.01) | |
| *A61K 38/09* | (2006.01) | |
| *A61K 38/16* | (2006.01) | |
| *A61K 38/17* | (2006.01) | |
| *A61K 38/18* | (2006.01) | |
| *A61K 38/25* | (2006.01) | |
| *A61K 38/29* | (2006.01) | |
| *A61K 38/30* | (2006.01) | |
| *A61K 38/48* | (2006.01) | |

(52) U.S. Cl.
CPC .............. *A61K 47/26* (2013.01); *A61K 9/0019* (2013.01); *A61K 9/19* (2013.01); *A61K 38/09* (2013.01); *A61K 38/16* (2013.01); *A61K 38/17* (2013.01); *A61K 38/1709* (2013.01); *A61K 38/1816* (2013.01); *A61K 38/22* (2013.01); *A61K 38/2207* (2013.01); *A61K 38/25* (2013.01); *A61K 38/26* (2013.01); *A61K 38/28* (2013.01); *A61K 38/29* (2013.01); *A61K 38/30* (2013.01); *A61K 38/4893* (2013.01); *A61K 47/02* (2013.01); *A61K 47/10* (2013.01); *A61K 47/12* (2013.01); *A61K 47/14* (2013.01); *A61K 47/183* (2013.01); *A61K 47/20* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 3,016,895 A | 1/1962 | Sein | 604/60 |
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,716,640 A | 2/1998 | Kamei et al. | 524/451 |
| 5,932,547 A * | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |

(Continued)

FOREIGN PATENT DOCUMENTS

| | | |
|---|---|---|
| EP | 0 916 347 | 5/1999 |
| EP | 1 502 589 | 2/2005 |

(Continued)

OTHER PUBLICATIONS

Autret, E. et al.: "Double-blind, randomized trial of diazepam versus placebo for prevention of recurrence of febrile seizures", *The Journal of Pediatrics*, vol. 117, No. 3, Sep. 1990, p. 490-494.
Amylin Agonists, from http://www.globalrph.com/amylin-agonists.htm, pp. 1-5, accessed Nov. 30, 2014.
Brown: "Clinicians' Guide to Diabetes Gadgets and Gizmos", *Clinical Diabetes*, 2008, 26, pp. 66-71.
DMSO Facts, from http://www.theundergroundcure.com/dmso-facts.html, p. 1, accessed Nov. 26, 2014.

(Continued)

*Primary Examiner* — Brian J Gangle
*Assistant Examiner* — Andrea McCollum
(74) *Attorney, Agent, or Firm* — Norton Rose Fulbright US LLP

(57) ABSTRACT

Stable formulations for parenteral injection of peptide drugs and methods of using such stable formulations are provided. In particular, the present invention provides stable formulations for parenteral injection of glucagon and methods of using such glucagon formulations to treat hypoglycemia, especially severe hypoglycemia in emergency situations.

27 Claims, 2 Drawing Sheets

(56) References Cited

U.S. PATENT DOCUMENTS

| | | | |
|---|---|---|---|
| 6,124,261 A | 9/2000 | Stevenson et al. | 514/2.4 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,371,939 B2 | 4/2002 | Bergens et al. | 604/156 |
| 6,495,164 B1 | 12/2002 | Ramstack et al. | 424/489 |
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |
| 7,314,636 B2 | 1/2008 | Caseres et al. | 424/426 |
| 7,371,406 B2 | 5/2008 | Rasstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,915,229 B2 | 3/2011 | Cohen et al. | 514/36 |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |
| 2004/0142043 A1 | 7/2004 | Maeda et al. | 524/499 |
| 2004/0176341 A1 | 9/2004 | Chou et al. | 514/179 |
| 2005/0019436 A1 | 1/2005 | Burch et al. | 424/760 |
| 2005/0069591 A1 | 3/2005 | Bernstein et al. | 424/489 |
| 2006/0160823 A1 | 7/2006 | Witchey-Lakshmanan et al. | 514/254.07 |
| 2006/0211982 A1 | 9/2006 | Prestrelski et al. | 604/60 |
| 2007/0196416 A1 | 8/2007 | Li et al. | 424/422 |
| 2008/0096967 A1 | 4/2008 | Lopez et al. | 514/567 |
| 2008/0132493 A1 | 6/2008 | Folger et al. | 514/224 |
| 2008/0145383 A1 | 6/2008 | Zauner et al. | 424/208.1 |
| 2008/0160067 A1 | 7/2008 | Boeckh et al. | 424/441 |
| 2008/0200383 A1 | 8/2008 | Jennings et al. | 514/11.3 |
| 2008/0220069 A1 | 9/2008 | Allison | 424/489 |
| 2008/0226689 A1 | 9/2008 | Berry et al. | 424/423 |
| 2008/0248999 A1 | 10/2008 | Steiner | 514/1.1 |
| 2008/0260840 A1 | 10/2008 | Alessi et al. | 514/12 |
| 2008/0305161 A1 | 12/2008 | Shah et al. | 424/456 |
| 2009/0215883 A1 | 8/2009 | Bouzada et al. | 514/449 |
| 2009/0226530 A1 | 9/2009 | Lassner et al. | 514/1.1 |
| 2009/0233912 A1 | 9/2009 | Castile et al. | 514/220 |
| 2010/0098735 A1 | 4/2010 | Jain et al. | 424/422 |
| 2010/0120660 A1 | 5/2010 | Balschmidt et al. | 514/1.1 |
| 2012/0046225 A1* | 2/2012 | Prestrelski et al. | 514/6.8 |

FOREIGN PATENT DOCUMENTS

| | | |
|---|---|---|
| EP | 2 060 268 | 5/2009 |
| GB | 2 119 248 | 11/1983 |
| WO | WO 91/16882 | 11/1991 |
| WO | WO 95/32730 | 12/1995 |
| WO | WO 96/09814 | 4/1996 |
| WO | WO 98/09613 | 3/1998 |
| WO | WO 98/16250 | 4/1998 |
| WO | WO 98/27963 | 7/1998 |
| WO | WO 00/16829 | 3/2000 |
| WO | WO 01/76682 | 10/2001 |
| WO | WO 01/78687 | 10/2001 |
| WO | WO 02/00137 | 1/2002 |
| WO | WO 02/49660 | 6/2002 |
| WO | WO 03/007782 | 1/2003 |
| WO | WO 03/041684 | 5/2003 |
| WO | WO 03/051398 | 6/2003 |
| WO | WO 2004/037242 | 5/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2006/031376 | 3/2006 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/045837 | 4/2009 |
| WO | WO 2009/060473 | 5/2009 |
| WO | WO 2009/070298 | 6/2009 |
| WO | WO 2010/018596 | 2/2010 |
| WO | WO 2011/154725 | 12/2011 |
| WO | WO 2012/012460 | 1/2012 |
| WO | WO 2012/122535 | 9/2012 |

OTHER PUBLICATIONS

Engeloch et al: "Stability of Screening Compounds in Wet DMSO", *Journal of Biomolecular Screening*, 2008, 13, pp. 999-1006.

Human insulin, from http://www.ncbi.nlm.nih.gov/protein/AAA59172.1, p. 1, accessed Nov. 26, 2014.

Knudsen, F Ursin; "Recurrence risk after first febrile seizure and effect of short term diazepam prophylaxis", *Archives of Disease in Childhood*, vol. 60, 1985 p. 1045-1049.

Pellock, John et al.: *Pediatric Epilepsy: Diagnosis and Therapy: Third Edition*—Chapter 19 "Febrile Seizures", 2008, p. 293-301.

Water, from http://www.biology-online.org/dictionary/Water, pp. 1-3, accessed Apr. 24, 2014.

Anderson et al., "Revised estimate of the prevalence of multiple sclerosis in the United States", *Ann. Neruol*, 31(3):333-336, 1992.

Arnon and Aharoni, "Neurogenesis and neuroprotection in the CNS—fundamental elements in the effect of Glatiramer acetate on treatment of autoimmune neurological disorders", Mol. Neurobiol., 36:245-253, 2007.

Bjartmar and Fox, "Pathological mechanisms and disease progression of multiple sclerosis: therapeutic implications", *Drugs of Today*, 38:17-29, 2002.

Bornstein et al., "A pilot trial of Cop 1 in exacerbateing remitting multiple sclerosis", New Eng. J. Med., 317:408-414,1987.

Bornstein et al., "A placebo-controlled, double-blind, randomized, two-center, pilot trial of Cop-1 in chronic progressive multiple sclerosis", Neurology, 41:533-539, 1991.

Bromberg, L. et al., "Transport of proteins dissolved in organic solvents across biomimetic membranes", *Proceedings of the National Academy of Sciences* 92(5):1262-1266, 1995.

Buffer Reference Center, from http;//www.sigmaaldrich.com/, pp. 1-7, accessed Jul. 3, 2013.

Cervera et al., "Mechanism of action of exenatide to reduce postprandial hyperglycemia in type 2 diabetes.", *Am J Physiol Endocrinol Metab* 294: E846-E852, 2008.

Chang et al., "Development of stable freeze-dried formulation of recombinant human interleukin-1 receptor antagonist", Pharm. Res., 13(2):243-249, 1996.

Comi & Filippi, "Treatment with glatiramer acetate delays conversion to clinically definiate multiple sclerosis (CDMS) in patients with clinically isolated syndromes (CIS)", Neurology, 71(2):153, 2008.

Comi et al, "Results from a phase III, one-year, randomized, double-blind, parallel-group, dosecomparison study with glatiramer acetate in relapsing-remitting multiple sclerosis", Mult. Scler., 14(suppl. 1):S299, 2008.

Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.

Compston et al., "The Story of Multiple Sclerosis" In: McAlpine's Multiple Sclerosis. London: Churchill Livingston, pp. 3-42, 2006.

Definition of analog, from http://cancerweb.ncl.ac.uk/cgi-bin/omd?query=analog, pp. 1-5, accessed Jul. 7, 2005.

DeLuca, "Freeze drying of pharmaceuticals", *J. Vac. Sci. Technol.*, 14(1):620, 1977.

Dhib-Jalbut, "Glatirmaer acetate (Copaxone) therapy for multiple sclerosis", Pharmacol Ther., 98:245-255,, 2003.

(56) References Cited

OTHER PUBLICATIONS

Dhib-Jalbut, "Mechanisms of action of interferons and glatiramer acetate in multiple sclerosis", Neurology, 25 58(Suppl 4):S3-S9, 2002.
Nash, "Suspensions", *Encyclopedia of Pharmaceutical Technology*, 6:3597-3610, 2007.
European Search Report for EP Appl. No. EP 12180169.0 dated Oct. 25, 2012.
Fleming and Carrithers, "Diagnosis and management of multiple sclerosis", Professional communications, Inc., 4 pages, 2002.
Geary et al., "Pancreatic Glucagon Fails to Inhibit Sham Feeding in the Rat", *Peptides*, vol. 1, 163-166, 1982.
Guideline on clinical investigation of medicinal products for the treatment of multiple sclerosis EMEA, London Sep. 16, 2006.
International Search Report and Written Opinion issued in PCT Application PCT/US2012/062816, dated Jan. 31, 2013.
International Search Report and Written Opinion issued in PCT Application PCT/US2013/048293, dated Aug. 8, 2013.
International Search Report and Written Opinion issued in PCT Application PCT/US2011/044576, dated Dec. 14, 2011.
International Search Report and Written Opinion issued in PCT Application PCT/US2012/028621, dated Aug. 22, 2012.
Johnson et al., "Extended use of glatiramer acetate (Copaxone) is well tolerated and maintains its clinical effect on multiple sclerosis relapse rate and degree of disability", Neurology, 50:701-708, 1998.
Kansara et al., "Subcutaneous delivery", *Drug. Deliv. Technol*, 9(6):38-42, 2009.
Meyer et al., "Preparation and in vitro characterization of gentamycin-impregnated biodegradable beads suitable for treatment of osteomyelitis", Journal of Pharmaceutical Sciences, 87(9):1149-1154, 1998.
Noseworthy et al, "Multiple sclerosis", *New Engl. J. Med.*, 343:938-952, 2000.
Rubino, *Solubilization of Some Poorly Soluble Drugs by Cosolvents*, PhD dissertation, The University of Arizona, 1984.
Ruggiere et al., "Glatiramer acetate in multiple sclerosis: A review", CNS Drug Reviews, 13(2):178-191, 2007.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Wang, "Lyophilization and development of solid protein pharmaceuticals", Int. J. Pharm., 203(1-2):1-60, 2000.
Weber et al., "Mechanism of action of glatiramer acetate in treatment of multiple sclerosis", *Neurotherapeutics*, 4(4):647-653, 2007.
Williams and Polli, "The lyophilization of pharmaceuticals: a literature review", *Journal of Parenteral Science and Technology*, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", *Adv. Neurol.*, pp. 273-292, 2006.
Ziemssen and Schrempf, "Glatiramer acetate: Mechanisms of action in multiple sclerosis", International Rev. of Neurobiol., 79:537-570, 2007.
Zacharis et al., "Volatile buffers can override the 'pH memory' of subtilisin catalysis in organic media", Proc. Natl. Acad. Sci. USA, 96(4):1201 1205, 1999.
Chang and Hershenson, "Practical Approaches to Protein Formulation Development", In: *Rationale Design of stable protein formulations-theory and practice*, pp. 1-25, 2002.
International Search Report and Written Opinion Issued in PCT Application No. PCT/US2014/015123, mailed Apr. 3, 2014.
Administer Intramuscular, Subcutaneous, and Intradermal Injections, from http://www.brooksidepress.org/Products/Administer_IM_SQ_and ID_Injections/lesson_1 . . . , pp. 1-3, published on 2007.
Buffer Reference Center, from http://sigmaaldrich.com/life-science/core-bioreagents/biological-buffers/learningcenter. Accessed Jul. 3, 2013.
Carpenter, et al., "Rational Design of Stable Lyophilized Protein Formulations: Theory and Practice." pp. 1-25. 2002.
Definition of mimetic, from http://www.merriam-webster.com/medical/mimetic, p. 1, accessed Jun. 26, 2014.
Diabetes Mellitus-Merck Manual, from http://www.merckmanuals.com/professional/print!endocrine_and_metabolic_disorders/diab . . . , pp. 1-22, accessed Apr. 2, 2013.
Glossary of medical education terms, Institute of International Medical Education. http://www.iime.org/glossary.htm. terms, Accessed in Mar. 2013.
Hypoglycemia-Merck Manual, from http://web.archive.org/web/20120115004118/http://www.merckmanuals.com/professional/ pp. 1-2, published on May 2007.
Iasemidis LD, "Epileptic Seizure Prediction and Control." IEEE Transac Biomed Eng. 50:549-558. 2003.
Izutsu, Stabilization of Therapeutic Proteins by Chemical and Physical Methods, pp. 287-292, from Therapeutic Proteins Methods and Protocols, Edited by C. Mark Smales and David C. James, published on 2005.
Vanderweele et al., "Glucagon, Satiety From Feeding and Liver/Pancreatic Interactions," Brain Research Bulletin, 17:539-543 (1986).

\* cited by examiner

STABLE FORMULATIONS FOR PARENTERAL INJECTION OF PEPTIDE DRUGS

CROSS-REFERENCES TO RELATED APPLICATIONS

This application is a divisional of U.S. application Ser. No. 13/417,073, filed Mar. 9, 2012, which claims priority to and the benefit of U.S. Provisional Application No. 61/451,568, filed Mar. 10, 2011, and entitled "Stable Formulations for Parenteral Injection of Peptide Drugs"; of U.S. Provisional Application No. 61/478,692, filed Apr. 25, 2011, and entitled "Stable Formulations for Parenteral Injection of Peptide Drugs"; of U.S. Provisional Application No. 61/553,388, filed Oct. 31, 2011, and entitled "Formulations for the Treatment of Diabetes"; and of and U.S. Provisional Application No. 61/609,123, filed Mar. 9, 2012, and entitled "Formulations for the Treatment of Diabetes," the entire disclosures of which are herein incorporated by reference for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The present invention relates to pharmaceutical formulations and, more particularly, to pharmaceutical formulations of peptides having improved stability and to methods of using such pharmaceutical formulations to treat various diseases, conditions and disorders.

BACKGROUND OF THE INVENTION

Diabetes is a serious health problem in modern society. Insulin is a critical treatment for both type I and type II diabetes. Studies over the past two decades have demonstrated that tight metabolic control of glucose through the use of insulin not only reduces the incidence, but also delays the development of complications in people with type 1 and type 2 diabetes. Unfortunately, the intensive insulin therapy required to achieve tight glucose control is also associated with a significantly increased risk of developing hypoglycemia or "low blood sugar."

Symptoms of hypoglycemia vary greatly among patients, but typically include tremor, palpitations, irritability, anxiety, nervousness, hunger, tachycardia, headache and pallor. The symptoms typically subside once plasma glucose is restored to normal levels. If hypoglycemia is not reversed, a further decrease in plasma glucose can lead to depletion of glucose in the central nervous system and associated neuroglycopenic symptoms, such as difficulty in concentration, slurred speech, blurred vision, reduction in body temperature, behavioral changes and, if not treated, unconsciousness, seizure and possibly death.

In general, hypoglycemia can be defined as minor to moderate hypoglycemia or as severe hypoglycemia as follows:

Minor to moderate hypoglycemia: Episodes that the patient can self-treat, regardless of the severity of symptoms, or any asymptomatic blood glucose measurements in which blood glucose levels are less than 70 mg/dL (3.9 mmol/L).

Severe hypoglycemia: Operationally defined as an episode of hypoglycemia that the patient cannot self-treat so that external help is required. Typically, neuroglycopenic symptoms and cognitive impairment begin at a blood glucose level of about 50 mg/dL (2.8 mmol/L).

Most episodes of minor to moderate hypoglycemia can be self-treated relatively easily by ingesting fast-acting carbohydrates such as glucose tablets or food (juice, soft drinks or sugary snacks). Severe hypoglycemia, by definition, cannot be self-treated and thus requires external intervention. If the patient can swallow and is cooperative, it is appropriate to use gels or products such as honey or jelly placed inside the cheek. If the patient is unable to swallow, glucagon, which is injected subcutaneously or intramuscularly, is used to treat severe hypoglycemia.

Glucagon is a naturally occurring peptide hormone that is 29 amino acids in length and is secreted by the a cells of the pancreas. The principal function of glucagon is to maintain glucose production through both glycogenolysis and gluconeogenesis, mostly mediated via the liver. Glucagon is the primary counter-regulatory hormone to insulin and is used as a first-line treatment of severe hypoglycemia in patients with diabetes.

Numerous attempts have been made to create a glucagon rescue medication for treating severe hypoglycemia in emergency situations. Currently, there are two glucagon kits currently available in the United States, manufactured by Eli Lilly (Glucagon Emergency Kit) and Novo Nordisk (GlucaGen® HypoKit). Both products combine a vial of freeze-dried glucagon with a pre-filled syringe of aqueous diluent. The freeze-dried glucagon must be reconstituted using a complex procedure that is difficult to use in an emergency situation. These products also provide a large volume injection because glucagon is poorly soluble in water. Recently, attempts have been made to improve the stability of glucagon in an aqueous solution, to create more stable glucagon analogs and/or to improve delivery of glucagon via powder injection.

Although some progress has been made, there still remains a need for a more user friendly glucagon rescue medication for treating severe hypoglycemia in emergency situations. Such a glucagon rescue medication would need to be carried continuously by diabetics and/or their caregivers and, thus, would need to be stable at nonrefrigerated temperatures (25-30° C.) for extended periods (>2 years). Ideally, it would also need to be simple to administer for the general population, and not require excessive processing/reconstitution prior to administration to the hypoglycemic patient. The glucagon rescue medication would also need to be functional over a range of temperatures, including temperatures ranging from 0° C.-30° C.

BRIEF SUMMARY OF THE INVENTION

To address such needs and others, the present invention provides a stable glucagon rescue formulation as well as methods of using this stable glucagon formulation to treat severe hypoglycemia. Advantageously, the glucagon is stabilized in the formulations of the present invention so as to allow for long-term storage and/or delivery over a prolonged period of time. As such, the glucagon formulations of the present invention are stable at nonrefrigerated temperatures for extended periods of time, are simple to administer, without the need for reconstitution, and are functional over a range of temperatures, including temperatures ranging from 0° C.-30° C.

Importantly, the formulation technology of the present invention is widely applicable for the delivery of numerous other peptides that, like glucagon, have poor or limited stability and solubility in an aqueous environment. In fact, it is now clear that the formulation of peptides with an aprotic polar solvent such as DMSO, NMP, ethyl acetate, or a mixture thereof into high concentration, nonaqueous solutions is a valuable delivery platform for this important class of peptide therapeutics. Additionally, the formulation technology of the present invention is widely applicable for the delivery of two or more peptides in the same solution.

Thus, in one aspect, the present invention provides a stable formulation for parenteral injection, the formulation comprising: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

In another aspect, the present invention provides a stable formulation for parenteral injection, the formulation comprising: (a) a first peptide or a salt thereof, wherein the first peptide has been dried in a first non-volatile buffer, and wherein the first dried peptide has a first pH memory that is about equal to the pH of the first peptide in the first non-volatile buffer; (b) a second peptide or a salt thereof, wherein the second peptide has been dried in a second non-volatile buffer, and wherein the second dried peptide has a second pH memory that is about equal to the pH of the second peptide in the second non-volatile buffer; and (c) an aprotic polar solvent; wherein the moisture content of the formulation is less than 5%, wherein the first dried peptide maintains the first pH memory that is about equal to the pH of the first peptide in the first non-volatile buffer when the first dried peptide is reconstituted in the aprotic polar solvent, and wherein the second dried peptide maintains the second pH memory that is about equal to the pH of the second peptide in the second non-volatile buffer when the second dried peptide is reconstituted in the aprotic polar solvent.

In another aspect, the present invention provides a stable formulation for parenteral injection, the formulation comprising: a peptide or a salt thereof (such as a hydrochloride or acetate salt thereof); and an aprotic polar solvent, wherein the moisture content of the formulation is less than 5%.

The stable formulations described herein are useful for the parenteral injection of any peptide that has limited or poor stability or solubility in an aqueous environment. Thus, in some embodiments, the peptide (or each of the first and second peptides) or salt thereof is selected from the group consisting of glucagon, pramlintide, insulin, leuprolide, an LHRH agonist, parathyroid hormone (PTH), amylin, botulinum toxin, hematide, an amyloid peptide, cholecystikinin, a conotoxin, a gastric inhibitory peptide, an insulin-like growth factor, a growth hormone releasing factor, an anti-microbial factor, glatiramer, glucagon-like peptide-1 (GLP-1), a GLP-1 agonist, exenatide, analogs thereof, and mixtures thereof. In a preferred embodiment, the peptide is glucagon or a glucagon analog or a glucagon peptidomimetic. In another embodiment, the peptide is parathyroid hormone. In yet another embodiment, the peptide is leuprolide. In still another embodiment, the peptide is glatiramer. In yet another embodiment, the first peptide is pramlintide and the second peptide is insulin. In still another embodiment, the first peptide is glucagon and the second peptide is exenatide.

The peptide (or, in embodiments where the formulation comprises two or more peptides, each of the peptides) is mixed with a non-volatile buffer and dried to a dry peptide powder. Suitable non-volatile buffers include, but are not limited to, glycine buffers, citrate buffers, phosphate buffers, and mixtures thereof. In one preferred embodiment, the non-volatile buffer is a glycine buffer. In another preferred embodiment, the non-volatile buffer is a mixture of citrate buffer and phosphate buffer. In some embodiments, wherein the formulation comprises two or more peptides, the first non-volatile buffer and the second non-volatile buffer are the same. In some embodiments, wherein the formulation comprises two or more peptides, the first non-volatile buffer and the second non-volatile buffer are different.

In some formulations of the present invention, the peptide is mixed with a non-volatile buffer and a stabilizing excipient, and then dried to a dry peptide powder. Suitable stabilizing excipients include, but are not limited to, sugars, starches, and mixtures thereof. In some embodiments, the sugar is trehalose. In some embodiments, the starch is hydroxyethyl starch (HES). In some embodiments, the stabilizing excipient is present in the formulation in an amount ranging from about 1% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, wherein the formulation comprises two peptides, both of the first peptide in the first non-volatile buffer and the second peptide in the second non-volatile buffer further comprise a stabilizing excipient, and the stabilizing excipient with the first peptide in the first non-volatile buffer and the stabilizing excipient with the second peptide in the second non-volatile buffer are the same. In other embodiments, wherein the formulation comprises two peptides, both of the first peptide in the first non-volatile buffer and the second peptide in the second non-volatile buffer further comprise a stabilizing excipient, and the stabilizing excipient with the first peptide in the first non-volatile buffer and the stabilizing excipient with the second peptide in the second non-volatile buffer are different.

Once the peptide or peptides and the non-volatile buffer or the peptide(s), the non-volatile buffer and the stabilizing excipient are dried to a powder, the dried peptide powder is dissolved or reconstituted in an aprotic polar solvent. Examples of aprotic polar solvents include, but are not limited to, the following: dimethylsulfoxide (DMSO), dimethylformamide (DMF), ethyl acetate, n-methyl pyrrolidone (NMP), dimethylacetamide (DMA), propylene carbonate, and mixtures thereof. Dimethylsulfoxide (DMSO), n-methyl pyrrolidone (NMP), ethyl acetate, and mixtures of one or more of DMSO, NMP, and ethyl acetate are particularly preferred aprotic polar solvents. In a preferred embodiment, the aprotic polar solvent is DMSO. In another preferred embodiment, the aprotic polar solvent is a mixture of DMSO and NMP. In yet another preferred embodiment, the aprotic polar solvent is a mixture of DMSO and ethyl acetate.

In some embodiments, the peptide or peptides are reconstituted in a mixture of an aprotic polar solvent (e.g., dimethylsulfoxide (DMSO), dimethylformamide (DMF), ethyl acetate, n-methyl pyrrolidone (NMP), dimethylacetamide (DMA), propylene carbonate, or mixtures thereof) and a co-solvent that depresses the freezing point of the formulation. In some embodiments, the co-solvent depresses the freezing point of the formulation by at least about 5° C., at least about 10° C., at least about 15° C., or at least about 20° C. In some embodiments, the co-solvent depresses the freezing point of the formulation to about 3° C., to about 2° C., to about 1° C., or to about 0° C. or below. In some embodiments, the co-solvent is a polar protic solvent. In preferred embodiments, the co-solvent is selected from ethanol, propylene glycol (PG), glycerol, and mixtures thereof. In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Importantly, the formulations of the present invention have very little residual moisture and, thus, the peptides in such formulations remain stable over extended periods of time. In preferred embodiments, the moisture content of the formulation of the present invention is less than about 4%, preferably, less than about 3%, preferably, less than about 2%, and even more preferably, less than about 1%, preferably, less than about 0.5%, preferably, less than about 0.25%, preferably, less than about 0.2%, preferably, less than about 0.15%, or preferably, less than about 0.1%. In other preferred embodiments, the moisture content of the formulation of the present invention is from about 0.01% to about 4%, preferably, from about 0.01% to about 3%, preferably, from about 0.01% to about 2%, preferably, from about 0.01% to about 1%, preferably, from about 0.1% to about 4%, preferably, from about 0.1% to about 3%, preferably, from about 0.1% to about 2%, preferably, from about 0.1% to about 1%, preferably, from about 0.25% to about 4%, preferably, from about 0.25% to about 3%, preferably, from about 0.25% to about 2%, preferably, from about 0.25% to about 1%, or preferably, from about 0.5% to about 1%.

When the peptide is mixed with a nonvolatile buffer, the nonvolatile buffer is selected such that the peptide has a pH of maximal stability, maximal solubility, and minimal degradation in the aqueous environment. Once dried, the peptide will have a pH memory of maximal stability, maximal solubility, and minimal degradation and will retain that pH memory when dissolved in or reconstituted in the aprotic polar solvent. As such, in preferred embodiments, the peptide in the formulation will have a pH memory of about 2.0 to about 3.0 to ensure maximal stability, maximal solubility, and minimal degradation. In other embodiments, the peptide in the formulation will have a pH memory of about 3.0 to about 5.0 to ensure maximal stability, maximal solubility, and minimal degradation. In other embodiments, the peptide in the formulation will have a pH memory of about 4.0 to about 5.0 to ensure maximal stability, maximal solubility, and minimal degradation. In yet other embodiments, the peptide will have a pH memory of about 4.0 to about 6.0 to ensure maximal stability, maximal solubility, and minimal degradation. In yet other embodiments, the peptide will have a pH memory of about 6.0 to about 8.0 to ensure maximal stability, maximal solubility, and minimal degradation. In some embodiments, wherein the formulation comprises two peptides, the first peptide has a pH memory of about 4.0 to about 6.0 to ensure maximal stability, maximal solubility, and minimal degradation, and the second peptide has a pH memory of about 1.5 to about 2.5, or of about 6.0 to about 8.0, to ensure maximal stability, maximal solubility, and minimal degradation. In some embodiments, wherein the formulation comprises two peptides, the first peptide has a pH memory of about 3.0 to about 5.0 to ensure maximal stability, maximal solubility, and minimal degradation, and the second peptide has a pH memory of about 1.5 to about 2.5, or of about 6.0 to about 8.0, to ensure maximal stability, maximal solubility, and minimal degradation. In other embodiments, wherein the formulation comprises two peptides, the first peptide has a pH memory of about 2.0 to about 3.0 to ensure maximal stability, maximal solubility, and minimal degradation, and the second peptide has a pH memory of about 4.0 to about 5.0 to ensure maximal stability, maximal solubility, and minimal degradation. It will be readily apparent to one of skill in the art how to determine the optimal pH for obtaining a peptide having maximal stability, maximal solubility, and minimal degradation.

Any suitable dosage of peptide or peptides can be formulated in the stable formulations of the present invention. Generally, the peptide (or, in embodiments comprising two or more peptides, each of the peptides) is present in the formulation in an amount ranging from about 0.5 mg/mL to about 100 mg/mL. In some embodiments, the peptide is present in the formulation in an amount ranging from about 10 mg/mL to about 60 mg/mL. In other embodiments, the peptide is present in the formulation in an amount ranging from about 20 mg/mL to about 50 mg/mL. In still other embodiments, the peptide is present in the formulation in an amount ranging from about 5 mg/mL to about 15 mg/mL. In yet other embodiments, the peptide is present in the formulation in an amount ranging from about 0.5 mg/mL to about 2 mg/mL. In yet other embodiments, the peptide is present in the formulation in an amount ranging from about 1 mg/mL to about 50 mg/mL. Again, it will be readily apparent to those of skill that the peptide dosage can be varied depending on the peptide used and the disease, disorder or condition to be treated.

In some embodiments, the formulations of the present invention further comprise an antioxidant. In other embodiments, the formulations further comprise a chelator. In still other embodiments, the formulations of the present invention further comprise a preservative.

In another aspect, the present invention provides a method for treating a disease, condition or disorder that may be treated, alleviated, or prevented by administering to a subject a stable peptide formulation as described herein in an amount effective to treat, alleviate or prevent the disease, condition, or disorder. In some embodiments, the disease, condition, or disorder is hypoglycemia. In some embodiments, wherein the disease, condition, or disorder is hypoglycemia, the method comprises administering a stable glucagon formulation of the present invention in an amount effective to treat the hypoglycemia. In some embodiments, the disease, condition, or disorder is diabetes. In some embodiments, wherein the disease, condition, or disorder is diabetes, the method comprises administering a stable insulin and pramlintide formulation of the present invention in an amount effective to treat the diabetes.

In yet another aspect, the present invention provides a process for making a stable formulation for parenteral injection, the process comprising: drying a peptide and a nonvolatile buffer to a dry peptide powder; and reconstituting the dry peptide powder with an aprotic polar solvent, thereby making the stable formulation, wherein the moisture content of the stable formulation is less than 5%. In some embodiments, the dried peptide powder has a pH memory that is about equal to the pH of the peptide in the non-volatile buffer, and the dried peptide powder maintains the pH memory that is about equal to the pH of the peptide in the non-volatile buffer when the dried peptide powder is reconstituted in the aprotic polar solvent.

In still another aspect, the present invention provides kits for treating a disease, condition or disorder, the kit comprising: a stable formulation comprising one or more peptides or salts thereof, wherein the peptide(s) has been dried in a non-volatile buffer, and wherein the dried peptide(s) has a pH memory that is about equal to the pH of the peptide(s) in the non-volatile buffer; and an aprotic polar solvent; wherein the moisture content of the formulation is less than 5%, and wherein the dried peptide(s) maintains the pH memory that is about equal to the pH of the peptide(s) in the non-volatile buffer when the dried peptide(s) is reconstituted in the aprotic polar solvent; and a syringe for administration of the stable formulation to the subject.

In some embodiments, the kit is for treating hypoglycemia and the stable formulation comprises a glucagon formulation as described herein. In some embodiments, the kit is for treating diabetes and the stable formulation comprises an insulin and pramlintide formulation as described herein. In some embodiments, the syringe is part of a pen injection device, an auto-injector device or a pump. In some embodiment, the syringe is prefilled with the stable formulation. In some embodiments, the kit further comprises instructions, wherein the instructions direct the administration of the stable formulation to treat the subject in need thereof.

Other objects, features, and advantages of the present invention will be apparent to one of skill in the art from the following detailed description and claims.

DETAILED DESCRIPTION OF THE INVENTION

I. Introduction

Figure 1:
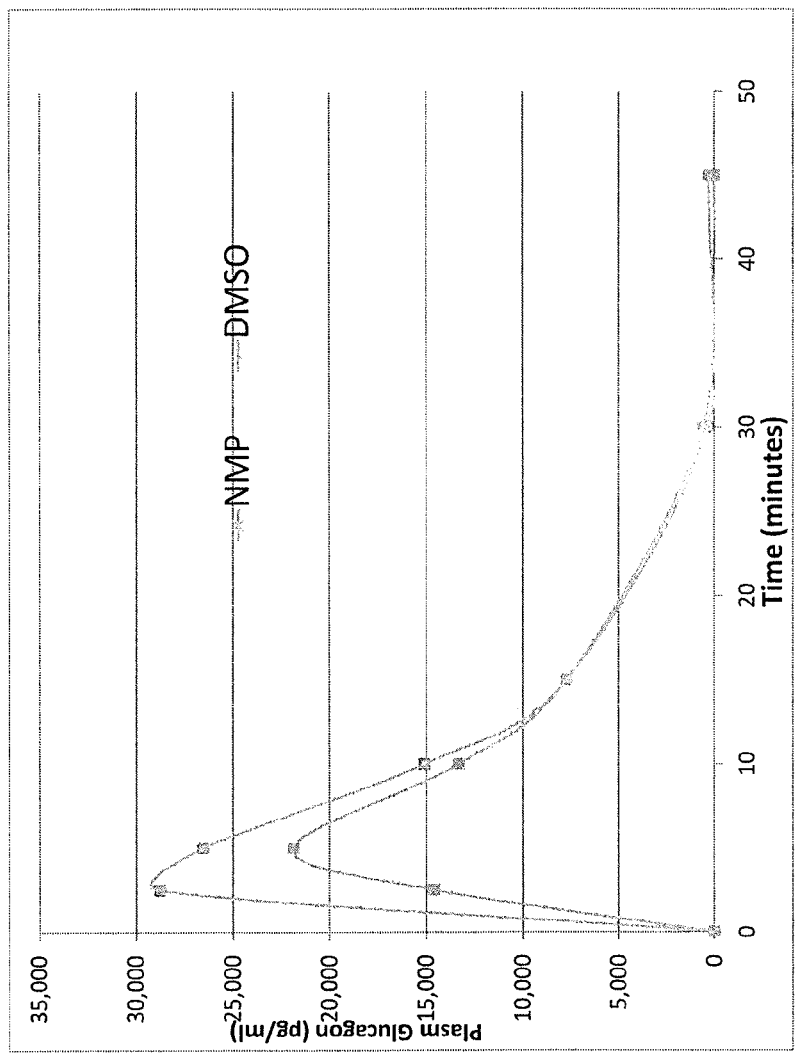
FIG. 1 illustrates plasma glucagon levels after injection of freeze-dried glucagon-glycine-trehalose dissolved in DMSO or NMP.

Peptides can degrade via a number of different mechanisms, including deamidation, oxidation, hydrolysis, disulfide interchange and racemization. Further, water acts as a plasticizer, which facilitates unfolding of protein molecules and irreversible molecular aggregation. Therefore, in order to provide a peptide formulation that is stable over time at ambient or physiological temperatures, a nonaqueous or substantially nonaqueous peptide formulation is generally required.

Reduction of aqueous peptide formulations to dry powdered formulations is one way to increase the stability of pharmaceutical peptide formulations. For example, peptide formulations can be dried using various techniques, including spray-drying, lyophilization or freeze-drying, and desiccation. The dry powder peptide formulations achieved by such techniques exhibit significantly increased stability over time at ambient or even physiological temperatures.

The present invention is based, in part, on the surprising discovery that a stable peptide formulation (e.g., a stable glucagon rescue formulation) can be readily prepared by first freeze-drying one or more peptides (e.g., a glucagon peptide) in a non-volatile buffer to a dry peptide powder. The dried peptide has a defined "pH memory" of the pH of the peptide in the non-volatile buffer from which the peptide was dried. Once dried, the resulting peptide powder, e.g., the freeze-dried glucagon, is dissolved in an aprotic polar solvent, thereby forming a stable formulation, wherein the moisture content of the formulation is less than 5% and, preferably, less than 4%, less than 3%, less than 2%, less than 1%, less than 0.5%, less than 0.25%, less than 0.15%, or less than 0.1%. The dried peptide maintains its defined pH memory when reconstituted in the aprotic polar solvent, i.e., the pH of the peptide when reconstituted in the aprotic polar solvent is about equal to the pH of the peptide in the non-volatile buffer from which it was dried. Advantageously, once prepared, the formulation (e.g., the glucagon formulation) is stable for extended periods of time, is ready for use without the need for reconstitution, and is functional over a range of temperatures.

Importantly, the formulation technology of the present invention is widely applicable for the delivery of numerous other peptides that, like glucagon, have poor or limited stability and solubility in an aqueous environment. In fact, it is now clear that formulation of peptides with an aprotic polar solvent (e.g., DMSO, NMP, ethyl acetate, or a mixture thereof) into high concentration, nonaqueous solutions is an invaluable delivery platform for an important class of therapeutic agents—therapeutic peptides. The stable formulations described herein advantageously promote uniform delivery of the peptide drugs and provide additional shelf stability against aggregation, oxidation, and hydrolysis related degradation pathways.

In certain preferred embodiments, the stable formulations described herein preserve the peptide drugs in a stable form for a prolonged period of time, e.g., for a period of time sufficient to provide a desired shelf life of the formulation without unacceptable levels of degradation of the therapeutic agent prior to use. A desired property of the injectable formulations is that they be nonaqueous and nonreactive with respect to the peptide. In such embodiments, it is possible to store the injectable formulations directly in the injection device itself.

The stable injectable formulations of the present invention contain the necessary delivered dose of therapeutic peptide or peptides (e.g., the dose required for drug therapy) and are preferably low volume. For example, in some embodiments an injectable formulation comprising a therapeutic dose of a peptide (e.g., glucagon) has a volume of at least about 1.0 microliters (the lower limit being a function of the filling equipment), more preferably from about 10 milliliters to about 250 microliters. The delivery of a therapeutic dose of peptide at a low volume is accomplished in certain preferred embodiments by concentrating the dose of the therapeutic peptide or peptides (e.g., glucagon) in a stable form in a suitable aprotic polar solvent for injection in accordance with the invention.

Furthermore, the stable formulations of the present invention are suitable for administration without requiring dilution prior to injection. Many currently available therapeutic peptide and vaccine products are produced in a solid particulate form to promote stability while on the shelf. These formulations are diluted prior to injection in sterile water, phosphate buffer solution, or isotonic saline. In contrast, in certain preferred embodiments of the present invention, the therapeutic peptide is concentrated using the particle preparation processing techniques (e.g., spray drying, lyophilization, etc.) routinely employed by the pharmaceutical industry to prepare formulations for injection. In preferred embodiments, therapeutic dosages of peptide drugs are achieved by dissolving the peptides, which have first been freeze-dried with a non-volatile buffer (and optionally additional components such as a stabilizing excipient) to a dried powder having very little residual moisture content. Once prepared, the dried peptide powder is dissolved in an aprotic polar solvent, such as DMSO, NMP, ethyl acetate, or blends of these solvents. Thus, in accordance with the goals of the present invention, the low volume, stable formulations of the present invention are injected, infused, or otherwise administered into an animal (e.g., human patient), without first diluting the formulation prior to injection as required by most reconstitution products. As such, in preferred embodiments, the low volume formulations of the present invention are administrable without being first being diluted, or reconstituted, or refrigerated.

II. Definitions

For purposes of the present disclosure, the following terms have the following meanings:

The term "therapeutic agent" encompasses peptide compounds together with pharmaceutically acceptable salts thereof. Useful salts are known to those skilled in the art and include salts with inorganic acids, organic acids, inorganic bases, or organic bases. Therapeutic agents useful in the present invention are those peptide compounds that affects a desired, beneficial, and often pharmacological, effect upon administration to a human or an animal, whether alone or in combination with other pharmaceutical excipients or inert ingredients.

The terms "peptide," "polypeptide" and/or "peptide compound" refer polymers of up to about 80 amino acid residues bound together by amide (CONH) linkages. Analogs, derivatives, agonists, antagonists and pharmaceutically acceptable salts of any of the peptide compounds disclosed here are included in these terms. The terms also include peptides and/or peptide compounds that have D-amino acids, modified, derivatized or normaturally occurring amino acids in the D- or L-configuration and/or peptomimetic units as part of their structure.

The term "pharmaceutically acceptable carrier" means a pharmaceutically acceptable solvent, suspending agent or vehicle for delivering a peptide compound of the present invention to a mammal such as an animal or human. In a presently preferred embodiment, the pharmaceutically acceptable carrier is an aprotic polar solvent.

The term "aprotic polar solvent" means a polar solvent that does not contain acidic hydrogen and does not act as a hydrogen bond donor. Examples of aprotic polar solvents include, but are not limited to, dimethylsulfoxide (DMSO), dimethylformamide (DMF), ethyl acetate, n-methyl pyrrolidone (NMP), dimethylacetamide (DMA), and propylene carbonate. The term aprotic polar solvent also encompasses mixtures of two or more aprotic polar solvents, e.g., a mixture of two or more of dimethylsulfoxide (DMSO), dimethylformamide (DMF), ethyl acetate, n-methyl pyrrolidone (NMP), dimethylacetamide (DMA), and propylene carbonate.

The term "pharmaceutically acceptable" ingredient, excipient or component is one that is suitable for use with humans and/or animals without undue adverse side effects (such as toxicity, irritation and allergic response) commensurate with a reasonable benefit/risk ratio.

The term "chemical stability" means that with respect to the therapeutic agent, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., room temperature); or storage of the product at 30° C./60% relative humidity for one year; or storage of the product at 40° C./75% relative humidity for one month, and preferably three months. In some embodiments, a chemically stable formulation has less than 20%, less than 15%, less than 10%, less than 5%, less than 4%, less than 3%, less than 2%, or less than 1% breakdown products formed after an extended period of storage at the intended storage temperature of the product.

The term "physical stability" means that with respect to the therapeutic agent, an acceptable percentage of aggregates (e.g., dimers, trimers and larger forms) is formed. In particular, a formulation is considered physically stable if no more that about 15% aggregates are formed after one year of storage at the intended storage temperature of the product (e.g., room temperature); or storage of the product at 30° C./60% relative humidity for one year; or storage of the product at 40° C./75% relative humidity for one month, and preferably three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

The term "stable formulation" means that at least about 65% chemically and physically stable therapeutic agent remains after two months of storage at room temperature. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta or electron beam).

The phrase "consisting essentially of" is used herein to exclude any elements that would substantially alter the essential properties of the stable formulations to which the phrase refers.

The term "bioavailability" is defined for purposes of the present invention as the extent to which the therapeutic agent, such as a peptide compound, is absorbed from the formulation.

The term "systemic" means, with respect to delivery or administration of a therapeutic agent, such as a peptide compound, to a subject, that therapeutic agent is detectable at a biologically significant level in the blood plasma of the subject.

The term "controlled release" is defined for purposes of the present invention as the release of the therapeutic agent at such a rate that blood (e.g., plasma) concentrations are maintained within the therapeutic range, but below toxic concentrations over a period of time of about one hour or longer, preferably 12 hours or longer.

The term "parenteral injection" refers to the administration of therapeutic agents, such as peptide compounds, via injection under or through one or more layers of skin or mucus membranes of an animal, such as a human. Standard parenteral injections are given into the intradermal, subcutaneous, or intramuscular region of an animal, e.g., a human patient. In some embodiments, a deep location is targeted for injection of a therapeutic agent as described herein.

The terms "treat" or "treatment" refer to delaying the onset of, retarding or reversing the progress of, or alleviating or preventing either the disease or condition to which the term applies, or one or more symptoms of such disease or condition.

The terms "patient," "subject," or "individual" interchangeably refer to a mammal, for example, a human or a non-human mammal, e.g., a primate, dog, cat, bovine, ovine, porcine, equine, mouse, rat, hamster, rabbit, or guinea pig.

III. Stable Peptide Formulations

In one aspect, the present invention provides a stable formulation for parenteral injection. Advantageously, once prepared, the formulation is stable for extended periods of time, is ready for use without the need for reconstitution, and is functional over a range of temperatures. Furthermore, the stable formulation of the present invention is useful for the parenteral injection of any peptide that has limited or poor stability or solubility in an aqueous environment. In some embodiments, the formulations of the present invention increase the physical stability of the peptide or peptides of the formulation, for example, by preventing or decreasing the formation of aggregates of the peptide or peptides.

In some embodiments, the formulation comprises: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

In some embodiments, the formulation comprises: (a) a first peptide or a salt thereof, wherein the first peptide has been dried in a first non-volatile buffer, and wherein the first dried peptide has a first pH memory that is about equal to the pH of the first peptide in the first non-volatile buffer; (b) a second peptide or a salt thereof, wherein the second peptide has been dried in a second non-volatile buffer, and wherein the second dried peptide has a second pH memory that is about equal to the pH of the second peptide in the second non-volatile buffer; and (c) an aprotic polar solvent; wherein the moisture content of the formulation is less than 5%, wherein the first dried peptide maintains the first pH memory that is about equal to the pH of the first peptide in the first non-volatile buffer when the first dried peptide is reconstituted in the aprotic polar solvent, and wherein the second dried peptide maintains the second pH memory that is about equal to the pH of the second peptide in the second non-volatile buffer when the second dried peptide is reconstituted in the aprotic polar solvent.

In some embodiments, the formulation consists essentially of: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent; wherein the moisture content of the formulation is less than 5%, and wherein the dried peptide maintains the pH memory that is about equal to the pH of the peptide in the non-volatile buffer when the dried peptide is reconstituted in the aprotic polar solvent.

A. Peptides

The stable formulations of the present invention comprise one, two, three, four, or more peptides or salts, analogs, and/or mixtures thereof. Peptides (as well as salts thereof) suitable for use in the formulations of the present invention include, but are not limited to, glucagon, pramlintide, insulin, leuprolide, an luteinizing-hormone-releasing hormone (LHRH) agonist, parathyroid hormone (PTH), amylin, botulinum toxin, hematide, an amyloid peptide, cholecystikinin, gastric inhibitory peptide, an insulin-like growth factor, growth hormone releasing factor, anti-microbial factor, glatiramer, glucagon-like peptide-1 (GLP-1), a GLP-1 agonist, exenatide, analogs thereof, and mixtures thereof. In some embodiments, the peptide is a hydrochloride salt or an acetate salt.

In a preferred embodiment, the peptide is glucagon or a glucagon analog or peptidomimetic, or a salt thereof (e.g., glucagon acetate). In another embodiment, the peptide is parathyroid hormone. In yet another embodiment, the peptide is leuprolide. In still another embodiment, the peptide is glatiramer. In other embodiments, the peptide is amylin or an amylinomimetic (e.g., pramlintide). In still other embodiments, the peptide is insulin or an insulin analog (e.g., Lispro). In some embodiments, the insulin or insulin analog preparation is a low-zinc or zinc-free preparation.

In some embodiments, the formulation comprises two peptides, wherein the first peptide is amylin or an amylinomimetic and the second peptide is insulin or an insulin analog. In some embodiments, the first peptide is pramlintide and the second peptide is insulin. In some embodiments, the first peptide is pramlintide and the second peptide is a low-zinc insulin preparation or a zinc-free insulin preparation.

In some embodiments, the formulation comprises two peptides, wherein the first peptide is glucagon and the second peptide is a glucagon-like peptide-1 (GLP-1) or a GLP-1 analog or agonist (e.g., exenatide). In some embodiments, the first peptide is glucagon and the second peptide is GLP-1. In some embodiments, the first peptide is glucagon and the second peptide is exenatide.

Any suitable dosage of peptide or peptides can be administered using the formulations of the present invention. The dosage administered will, of course, vary depending upon known factors, such as the pharmacodynamic characteristics of the particular peptide, salt, or combination thereof; the age, health, or weight of the subject; the nature and extent of symptoms; the metabolic characteristics of the therapeutic agent and patient, the kind of concurrent treatment; the frequency of treatment; or the effect desired. Generally, the peptide (or, wherein the stable formulation comprises two or more peptides, each of the peptides) is present in the formulation in an amount ranging from about 0.5 mg/mL to about 100 mg/mL (e.g., about 0.5, 1, 2, 3, 4, 5, 6, 7, 8, 9, 10, 15, 20, 25, 30, 35, 40, 45, 50, 55, 60, 65, 70, 75, 80, 85, 90, 95, or 100 mg/mL).

In some embodiments, the peptide is present in the formulation in an amount ranging from about 0.5 mg/mL to about 60 mg/mL. In some embodiments, the peptide is present in the formulation in an amount ranging from about 10 mg/mL to about 50 mg/mL. In other embodiments, the peptide is present in the formulation in an amount ranging from about 20 mg/mL to about 50 mg/mL. In still other embodiments, the peptide is present in said formulation in an amount ranging from about 5 mg/mL to about 15 mg/mL. In yet other embodiments, the peptide is present in the formulation in an amount ranging from about 0.5 mg/mL to about 2 mg/mL. Again, it will be readily apparent to those of skill that the peptide dosage can be varied depending on the peptide used and the disease, disorder or condition to be treated.

In preferred embodiments, the peptide is mixed with a non-volatile buffer, and optionally a stabilizing excipient, and then dried to a dry peptide powder. In embodiments where the stable formulation comprises two or more peptides, each of the peptides is separately mixed with a non-volatile buffer, and optionally a stabilizing excipient, and then dried to a dry peptide powder. Peptides are susceptible to hydrolysis at bonds with asparagine residues and oxidation of methionine, so the use of non-volatile buffers in the formulations of the present invention beneficially affects chemical stability. As described in further detail below, while pH is not relevant in an aprotic polar solvent, the charge profile of a peptide in an aprotic polar solvent will affect its stability. The charge profile of a peptide in an aprotic polar solvent will be a function of the pH of the aqueous solution from which it was previously dried, i.e., there is a "pH memory" after dissolution or reconstitution in an aprotic polar solvent. To achieve the desired charge profile for a peptide dissolved in an aprotic polar solvent, the peptide is dried from a buffered aqueous solution at the pH that yields the optimal stability, optimal solubility, and minimal degradation in the aprotic polar solvent.

As such, non-volatile buffers that are useful in the formulations described herein are those that are helpful in establishing a pH of maximum stability, maximum solubility, and minimal degradation as well as those that are helpful in removing residual moisture or water content from the dried peptide powder. Non-volatile buffers include those buffers that will not evaporate away in a manner similar to water upon drying/lyophilization. Suitable non-volatile buffers include, for example, glycine buffers, citrate buffers, phosphate buffers, and mixtures thereof. In some embodiments, the non-volatile buffer is a glycine buffer or a citrate buffer. In some embodiments, the non-volatile buffer is a glycine buffer. In some embodiments, the non-volatile buffer is a mixture of glycine buffer and citrate buffer. In some embodiments, the non-volatile buffer is a mixture of citrate buffer and phosphate buffer.

B. Stabilizing Excipients

In certain preferred embodiments, the formulations described herein may be further stabilized to ensure the stability of the peptide incorporated therein. In some embodiments, the stability of the injectable formulation is enhanced by the inclusion of one or more stabilizing agents or stabilizing excipients into the formulation prior to the drying of the peptide or peptides. In other embodiments, the stability of the injectable formulation is enhanced by reconstituting the dried peptide or peptides with a stabilizing agent or stabilizing excipient in the aprotic polar solvent.

In some embodiments, the stabilizing excipient is a cryoprotectant. As shown below in the Examples section, the addition of a cryoprotectant, such as trehalose, protects the peptide formulations of the present invention against instability associated with freeze-thaw cycles. Furthermore, it has been shown herein that the addition of the cryoprotectant trehalose also promotes enhanced thawing of a frozen peptide formulation. This property of enhanced thawing is surprisingly advantageous, particularly in emergency medical situations, such as a severe hypoglycemia episode, wherein a peptide formulation of the present invention is frozen and needs to be administered quickly. Thus, in another aspect of the present invention, the stable formulation has an improved freeze-thaw stability, an enhanced thawing rate, and/or an enhanced thawing profile.

In some embodiments, the stabilizing excipient is selected from sugars, starches, sugar alcohols, and mixtures thereof. Examples of suitable sugars for stabilizing excipients include, but are not limited to, trehalose, glucose, sucrose, etc. Examples of suitable starches for stabilizing excipients include, but are not limited to, hydroxyethyl starch (HES). Examples of suitable sugar alcohols for stabilizing excipients include, but are not limited to, mannitol and sorbitol. In some embodiments, the at least one stabilizing excipient (e.g., a sugar, a starch, a sugar alcohol, or a mixture thereof) is capable of enhancing the stability of the peptide during a freeze-thawing process, enhancing the thawing rate of the formulation, or enhancing the thawing profile of the formulation.

In some embodiments, the stabilizing excipient is present in the formulation in an amount ranging from about 1% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the stabilizing excipient is present in the formulation in an amount that is about 1%, about 5%, about 10%, about 15%, about 20%, about 25%, about 30%, about 35%, about 40%, about 45%, about 50%, about 55%, or about 60% (w/v).

In formulations comprising two or more peptides, in some embodiments each of the peptides are dried in a mixture comprising a non-volatile buffer and a stabilizing excipient. The mixtures of the non-volatile buffer and the stabilizing excipient may be the same for each peptide, or the non-volatile buffer, the stabilizing excipient, or both the non-volatile buffer and stabilizing excipient that is used for drying each peptide may be different. In other embodiments, some but not all of the peptides may be dried in a mixture comprising a non-volatile buffer and a stabilizing excipient, while other peptides may be dried in a non-volatile buffer in the absence of a stabilizing excipient.

In some embodiments, the formulation further comprises additional stabilizing agents including, for example, antioxidants, chelators and preservatives. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, tartaric acid and salts thereof, glycerin, and citric acid and salts thereof. Examples of suitable preservatives include, but are not limited to, benzyl alcohols, methyl parabens, propyl parabens, and mixtures thereof.

In some embodiments, the formulation further comprises a stabilizing polyol. Such formulations and materials are described, for example, in U.S. Pat. Nos. 6,290,991 and 6,331,310, the contents of each of which are incorporated by reference herein.

C. Reconstitution of Dried Peptides

In the stable formulations of the present invention, once the peptide and non-volatile buffer (and optionally the stabilizing excipient) are dried to a powder, or where the formulation comprises two or more peptides, once each of the peptide and non-volatile buffer (each optionally also comprising a stabilizing excipient) is dried to a powder, the dried peptide powder is, or the dried peptide powders are, dissolved or reconstituted in an aprotic polar solvent. In some embodiments, the aprotic polar solvent is selected from dimethylsulfoxide (DMSO), dimethylformamide (DMF), ethyl acetate, n-methyl pyrrolidone (NMP), dimethylacetamide (DMA), propylene carbonate, and mixtures thereof. In some embodiments, the aprotic polar solvent is a mixture of two or more of dimethylsulfoxide (DMSO), dimethylformamide (DMF), ethyl acetate, n-methyl pyrrolidone (NMP), dimethylacetamide (DMA), and propylene carbonate. Dimethylsulfoxide (DMSO), ethyl acetate, and n-methyl pyrrolidone (NMP) are particularly preferred aprotic polar solvents, each of which is a biocompatible solvent. In some embodiments, the aprotic polar solvent is dimethylsulfoxide (DMSO). In other embodiments, the aprotic polar solvent is n-methyl pyrrolidone (NMP). In other embodiments, the aprotic polar solvent is a mixture of dimethylsulfoxide (DMSO) and n-methyl pyrrolidone (NMP). In still other embodiments, the aprotic polar solvent is a mixture of dimethylsulfoxide (DMSO) and ethyl acetate. In some embodiments, the dried peptide powder is reconstituted in an aprotic polar solvent that is "neat," i.e., that does not contain a co-solvent. In some embodiments, the dried peptide powder is reconstituted in a solution that comprises an aprotic polar solvent and that does not contain water as a co-solvent.

In some embodiments, the formulations of the present invention further comprise at least one co-solvent that depresses the freezing point of the formulation. The co-solvent is a polar protic solvent. In some embodiment, the co-solvent is selected from ethanol, propylene glycol (PG), glycerol, and mixtures thereof. In some embodiments, the co-solvent is ethanol or propylene glycol (PG). The co-solvent may be present in the formulation in an amount ranging from about 10% (w/v) to about 50% (w/v), e.g., about 10%, about 15%, about 20%, about 25%, about 30%, about 35%, about 40%, about 45%, or about 50% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v). In some embodiments, the at least one co-solvent depresses the freezing point of the formulation by at least 5° C., at least 10° C., at least 15° C., at least 20° C. or more as compared to an otherwise identical formulation that does not comprise the co-solvent. In some embodiments, the at least one co-solvent depresses the freezing point of the formulation to about 3° C., to about 2° C., to about 1° C., or about 0° C. or below.

D. Moisture Content

The formulations of the present invention have very little residual moisture and, thus, the peptides in such formulations remain stable over extended periods of time. In some embodiments, the stable formulations of the present invention have a moisture content that is less than 5%. In some embodiments, the moisture content is less than 4%, less than 3%, less than 2%, less than 1%, less than 0.5%, less than 0.4%, less than 0.3%, less than 0.25%, less than 0.2%, less than 0.15%, less than 0.1%, less than 0.075%, less than 0.05%, less than 0.025%, or less than 0.01%. In some preferred embodiments, the moisture content of the formulations of the present invention is from about 0.01% to about 5%, from about 0.01% to about 4%, from about 0.01% to about 3%, from about 0.01% to about 2%, from about 0.01% to about 1.5%, or from about 0.01% to about 1%. In other preferred embodiments, the moisture content of the formulations of the present invention is from about 0.1% to about 5%, from about 0.1% to about 4%, from about 0.1% to about 3%, from about 0.1% to about 2%, from about 0.1% to about 1.5%, or from about 0.1% to about 1%. In other preferred embodiments, the moisture content of the formulations of the present invention is from about 0.25% to about 5%, from about 0.25% to about 4%, from about 0.25% to about 3%, from about 0.25% to about 2%, or from about 0.25% to about 1.5%. In still other preferred embodiments, the moisture content of the formulations is from about 0.5% to about 1%.

E. pH Memory

The "pH memory" of a peptide is the resulting charge profile (protonation state) after drying the peptide from a buffered aqueous solution (e.g., from a non-volatile buffer). The protonation state, and thus the solubility and stability of peptides, in very low or zero moisture non-aqueous solvents are affected by the aqueous pH of the peptide solution before drying and the drying conditions employed. When the peptide is dried in a buffer species in which both the acidic and basic components are non-volatile, the pH memory of the dried peptide will be about equal to the pH of the peptide in the non-volatile buffer. See, e.g., *Enzymatic Reactions in Organic Media*, Koskinen, A. M. P., and Klibanov, A. M., eds., Springer (1996). Furthermore, the pH of the buffered aqueous solution (e.g., non-volatile buffer) in which the peptide is dried can be optimized to yield a pH memory for the peptide that results in optimal peptide stability, maximum solubility, and minimal degradation when the dried peptide is subsequently reconstituted in an aprotic polar solvent. Because aprotic polar solvents do not have exchangeable protons, when the dried peptide is reconstituted into an aprotic polar solvent, the reconstituted formulation will maintain the solubility and stability characteristics of the optimal pH memory.

For stable formulations comprising two, three, four, or more peptides, each peptide is dried so that it has its own pH memory that is optimized for maximum solubility, maximum stability, and minimal degradation. In embodiments where there are two or more peptides in the formulation, the pH memory range of the first peptide may partially overlap with the pH memory range of the second peptide (e.g., the pH memory of the first peptide may be from about 4.0 to about 6.0, and the pH memory of the second peptide may be from about 6.0 to about 8.0), or the pH memory range of the first peptide may not overlap with the pH memory range of the second peptide (e.g., the pH memory of the first peptide may be from about 4.0 to about 5.0, and the pH memory of the second peptide may be from about 6.0 to about 8.0).

The pH memory of a peptide can be measured in several ways. In one method, the pH memory of a peptide is measured by reconstituting the dried peptide into un-buffered water and measuring the pH of the reconstituted peptide with a pH indicator such as pH paper or a calibrated pH electrode. Alternatively, the pH memory of a peptide can be determined for a peptide that has been reconstituted in the aprotic polar solvent (e.g., DMSO) by adding at least 20% water to the aprotic polar solvent (e.g., DMSO) and measuring the pH with a pH indicator. See, e.g., Baughman and Kreevoy, "Determination of Acidity in 80% Dimethyl Sulfoxide-20% Water," *Journal of Physical Chemistry*, 78(4):421-23 (1974). Measurement of pH in an aprotic polar solvent-water solution may require a small correction (i.e., no more than 0.2 pH unit as per Baughman and Kreevoy, supra).

In some embodiments, a dried peptide has a pH memory that is about equal to the pH of the peptide in the non-volatile buffer from which it was dried when the pH memory of the peptide when it is reconstituted in an aprotic polar solvent is within one pH unit of the pH of the peptide in the non-volatile buffer from which it is dried (thus, for example, for a peptide having a pH of 3.0 in the non-volatile buffer from which the peptide is dried, a pH memory for the peptide of from 2.0 to 4.0, when reconstituted in the aprotic polar solvent, would be within one pH unit, and thus the pH memory of the dried peptide would be about equal to the pH of the peptide in the non-volatile buffer). In some embodiments, a dried peptide has a pH memory that is about equal to the pH of the peptide in the non-volatile buffer from which it was dried when the pH memory of the peptide when it is reconstituted in an aprotic polar solvent is within half of a pH unit of the pH of the peptide in the non-volatile buffer from which it is dried (thus, for example, for a peptide having a pH of 3.0 in the non-volatile buffer from which the peptide is dried, a pH memory for the peptide of from 2.5 to 3.5, when reconstituted in the aprotic polar solvent, would be within half of a pH unit, and thus the pH memory of the dried peptide would be about equal to the pH of the peptide in the non-volatile buffer).

In some embodiments, the peptide of the stable formulation has a pH memory of about 1.5 to about 2.5. In some embodiments, the peptide of the stable formulation has a pH memory of about 2.0 to about 3.0. In some embodiments, the peptide of the stable formulation has a pH memory of about 2.0 to about 4.0. In some embodiments, the peptide of the stable formulation has a pH memory of about 2.5 to about 4.0. In some embodiments, the peptide of the stable formulation has a pH memory of about 2.5 to about 3.5. In some embodiments, the peptide of the stable formulation has a pH memory of about 3.0 to about 5.0. In some embodiments, the peptide of the stable formulation has a pH memory of about 3.0 to about 4.5. In some embodiments, the peptide of the stable formulation has a pH memory of about 4.0 to about 5.0. In some embodiments, the peptide of the stable formulation has a pH memory of about 4.0 to about 6.0. In some embodiments, the peptide of the stable formulation has a pH memory of about 6.0 to about 8.0. In some embodiments, the peptide of the stable formulation has a pH memory of about 6.5 to about 8.0. In some embodiments, the peptide of the stable formulation has a pH memory of about 6.5 to about 7.5. In some embodiments, the peptide of the stable formulation has a pH memory of about 6.5 to about 9.0. In some embodiments, the peptide of the stable formulation has a pH memory of about 7.0 to about 9.0. In some embodiments, the peptide of the stable formulation has a pH memory of about 7.5 to about 9.0. In some embodiments, the peptide of the stable formulation has a pH memory of about 8.0 to about 10.0. In some embodiments, the peptide of the stable formulation has a pH memory of about 8.5 to about 10.0. In some embodiments, the pH memory of a peptide may be about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, or about 10.0.

F. Exemplary Formulations

In some particular embodiments, the present invention provides a stable glucagon formulation, the glucagon formulation comprising: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent. In some embodiments, the glucagon is present in the formulation in an amount ranging from about 0.5 mg/mL to about 100 mg/mL, or from about 1 mg/mL to about 50 mg/mL. In some embodiments, the moisture content of the formulation is less than about 2%, less than about 1%, less than about 0.5%, or less than about 0.01%. In some embodiments, the moisture content of the formulation is from about 0.01% to about 3%. In some embodiments, the formulation further comprises a stabilizing excipient selected from sugars (e.g., trehalose), starches (e.g., hydroxyethyl starch (HES)), and mixtures thereof. The stabilizing excipient may be present in the formulation in an amount ranging from about 1% (w/v) to about 60% (w/v). In some embodiments, the formulation further comprises a co-solvent that depresses the freezing point of the formulation, wherein the co-solvent is selected from ethanol, propylene glycol, glycerol, and mixtures thereof. The co-solvent may be present in the formulation in an amount ranging from about 10% (w/v) to about 50% (w/v).

In other particular embodiments, the present invention provides a stable glucagon formulation, the glucagon formulation comprising: a glucagon peptide or salt thereof (or glucagon analog or peptidomimetic); and an aprotic polar solvent selected from the group consisting of dimethylsulfoxide (DMSO), n-methyl pyrrolidone (NMP) and mixtures thereof; wherein the moisture content of the formulation is less than 3%. In preferred embodiments, the moisture content of the formulation is less than 2%, less than 1%, less than 0.5% and less than 0.25%. In other preferred embodiments, the moisture content is from 0.25% to about 3%, preferably from about 0.25% to about 2%, more preferably from about 0.25% to about 1.5%, more preferably from about 0.25% to about 1%, more preferably from about 0.5% to about 1%.

In other particular embodiments, the stable glucagon formulation further comprises a non-volatile buffer and a stabilizing excipient that is a sugar, a starch, or a sugar alcohol. For instance, in some embodiments, the glucagon formulation further comprises a glycine buffer and mannitol, or a citrate buffer and mannitol, or a phosphate buffer and mannitol. In some embodiments, the glucagon formulation further comprises a glycine buffer and trehalose, or a citrate buffer and trehalose, or a phosphate buffer and trehalose. In these embodiments, the aprotic polar solvent can be DMSO, NMP, ethyl acetate, or a mixture thereof. For instance, in one preferred embodiment, the aprotic polar solvent is DMSO, and the non-volatile buffer is a glycine buffer. In another preferred embodiment, the aprotic polar solvent is DMSO, the non-volatile buffer is a citrate buffer and the stabilizing excipient is mannitol. In another preferred embodiments, the aprotic polar solvent is DMSO, the non-volatile buffer is a glycine buffer, and the stabilizing excipient is trehalose. In still another preferred embodiment, the aprotic polar solvent is DMSO, and the non-volatile buffer is a citrate buffer. In still another preferred embodiment, the aprotic polar solvent is NMP, and the non-volatile buffer is a glycine buffer.

In other particular embodiments, the present invention provides a stable formulation comprising: glucagon or a salt thereof (e.g., glucagon acetate), wherein the glucagon has been dried in a non-volatile buffer, and wherein the dried glucagon has a pH memory that is about equal to the pH of the glucagon in the non-volatile buffer selected from a glycine buffer, a citrate buffer, a phosphate buffer, and mixtures thereof, wherein the pH memory of the dried glucagon is from about 2.0 to about 3.0; and an aprotic polar solvent selected from dimethylsulfoxide (DMSO), n-methyl pyrrolidone (NMP), ethyl acetate, and mixtures thereof; wherein the moisture content of the formulation is less than 1%, and wherein the dried glucagon maintains the pH memory that is about equal to the pH of the glucagon in the non-volatile buffer when the dried glucagon is reconstituted in the aprotic polar solvent. In some embodiments, the glucagon formulation further comprises a co-solvent that depresses the freezing point of the formulation, wherein the co-solvent is selected from ethanol, propylene glycol, glycerol, and mixtures thereof. In some embodiments, the glucagon formulation further comprises a stabilizing excipient selected from sugars, starches, and mixtures thereof. In some embodiments, the glucagon is present in the formulation in an amount ranging from about 1 mg/mL to about 50 mg/mL.

In other particular embodiments, the present invention provides a stable glucagon formulation, the glucagon formulation consisting essentially of: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In still other particular embodiments, the present invention provides a stable glucagon formulation, the glucagon formulation consisting essentially of: a glucagon peptide or salt thereof (e.g., glucagon acetate), wherein the glucagon has been dried in a non-volatile buffer selected from a glycine buffer, a citrate buffer, a phosphate buffer, and mixtures thereof, and wherein the dried glucagon has a pH memory that is from about 2.0 to about 3.0; and a mixture of an aprotic polar solvent and a co-solvent that depresses the freezing point of the formulation, wherein the aprotic polar solvent is selected from the group consisting of dimethylsulfoxide (DMSO), ethyl acetate, n-methyl pyrrolidone (NMP), and mixtures thereof and wherein the co-solvent is selected from ethanol, propylene glycol, glycerol, and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In other particular embodiments, the present invention provides a stable glucagon formulation, the glucagon formulation consisting essentially of: a glucagon peptide or salt thereof (e.g., glucagon acetate), wherein the glucagon has been dried in a mixture of a non-volatile buffer and a stabilizing excipient, wherein the non-volatile buffer is selected from a glycine buffer, a citrate buffer, a phosphate buffer, and mixtures thereof, and the stabilizing excipient is selected from sugars (e.g., trehalose), starches (e.g., hydroxyethyl starch (HES)), and mixtures thereo, and wherein the dried glucagon has a pH memory that is from about 2.0 to about 3.0; and an aprotic polar solvent selected from the group consisting of dimethylsulfoxide (DMSO), ethyl acetate, n-methyl pyrrolidone (NMP), and mixtures thereof; wherein the moisture content of the formulation is less than 5%, and wherein the dried glucagon maintains the pH memory of about 2.0 to about 3.0 when the dried glucagon is reconstituted in the aprotic polar solvent.

In still other particular embodiments, the present invention provides a stable formulation comprising: insulin, wherein the insulin has been dried in a first non-volatile buffer selected from a glycine buffer, a citrate buffer, a phosphate buffer, and mixtures thereof, and wherein the dried insulin has a first pH memory that is about equal to the pH of the insulin in the first non-volatile buffer, wherein the first pH memory is from about 1.5 to about 2.5, or from about 6.0 to about 8.0; pramlintide, wherein the pramlintide has been dried in a second non-volatile buffer selected from a glycine buffer, a citrate buffer, a phosphate buffer, and mixtures thereof, and wherein the dried pramlintide has a second pH memory that is about equal to the pH of the pramlintide in the second non-volatile buffer, wherein the second pH memory is from about 3.0 to about 5.0, or from about 4.0 to about 6.0; and an aprotic polar solvent selected from dimethylsulfoxide (DMSO), n-methyl pyrrolidone (NMP), ethyl acetate, and mixtures thereof; wherein the moisture content of the formulation is less than 1%, wherein the dried insulin maintains the first pH memory that is about equal to the pH of the insulin in the first non-volatile buffer when the dried insulin is reconstituted in the aprotic polar solvent, and wherein the dried pramlintide maintains the second pH memory that is about equal to the pH of the pramlintide in the second non-volatile buffer when the dried pramlintide is reconstituted in the aprotic polar solvent. In some embodiments, the insulin and pramlintide formulation further comprises a co-solvent that depresses the freezing point of the formulation, wherein the co-solvent is selected from ethanol, propylene glycol, glycerol, and mixtures thereof. In some embodiments, one or both of the insulin in the first non-volatile buffer and the pramlintide in the second non-volatile buffer further comprises a stabilizing excipient selected from sugars, starches, and mixtures thereof. In some embodiments, the first non-volatile buffer and the second non-volatile buffer are the same. In some embodiments, the first non-volatile buffer and the second non-volatile buffer are different. In some embodiments, each of the insulin and pramlintide is present in the formulation in an amount ranging from about 1 mg/mL to about 50 mg/mL. In some embodiments, the first pH memory is from about 1.5 to about 2.5. In some embodiments, the first pH memory is from about 6.0 to about 8.0. In some embodiments, the second pH memory is from about 3.0 to about 5.0. In some embodiments, the second pH memory is from about 4.0 to about 6.0. In some embodiments, the first pH memory is from about 1.5 to about 2.5 and the second pH memory is from about 3.0 to about 5.0.

IV. Methods of Making Stable Peptide Formulations

In yet another aspect, the present invention provides a process for making a stable formulation for parenteral injection. In some embodiments, the process comprises: drying a peptide and a non-volatile buffer to a dry peptide powder; and reconstituting the dried peptide powder with an aprotic polar solvent, thereby making the stable formulation, wherein the moisture content of the stable formulation is less than 5%. In some embodiments, the dried peptide powder has a pH memory that is about equal to the pH of the peptide in the non-volatile buffer, and the dried peptide powder maintains the pH memory that is about equal to the pH of the peptide in the non-volatile buffer when the dried peptide powder is reconstituted in the aprotic polar solvent.

The process for making stable peptide formulations can be used to formulate any peptide that has limited or poor stability or solubility in an aqueous environment. Peptides (or salts thereof) suitable for use in the formulations of the present invention include, but are not limited to, glucagon, insulin, leuprolide, an luteinizing-hormone-releasing hormone (LHRH) agonists, pramlintide, parathyroid hormone (PTH), amylin, botulinum toxin, a conotoxin, hematide, an amyloid peptide, cholecystikinin, gastric inhibitory peptide, an insulin-like growth factor, growth hormone releasing factor, antimicrobial factor, glatiramer, glucagon-like peptide-1 (GLP-1), a GLP-1 agonist, exenatide, and analogs thereof. In a preferred embodiment, the peptide is glucagon or a glucagon analog or peptidomimetic. In another embodiment, the peptide is parathyroid hormone. In yet another embodiment, the peptide is leuprolide. In still another embodiment, the peptide is glatiramer.

In some embodiments, two, three, four or more peptides are formulated into a stable formulation. In embodiments where two or more peptides are formulated into the stable formulation, each peptide is separately dried with a non-volatile buffer to a dry peptide powder, and each dried peptide powder has a pH memory that is about equal to the pH of the peptide in the non-volatile buffer (i.e., the first peptide has a first pH memory that is about equal to the pH of the first peptide in the first non-volatile buffer, and the second peptide has a second pH memory that is about equal to the pH of the second peptide in the second non-volatile buffer). The two or more dried peptide powders are reconstituted with an aprotic polar solvent, thereby making the stable formulation, wherein the moisture content of the stable formulation is less than 5%, and wherein each dried peptide powder maintains the pH memory that is about equal to the pH of the peptide in the non-volatile buffer when the dried peptide powder is reconstituted in the aprotic polar solvent (i.e., the first dried peptide maintains the first pH memory when the first dried peptide is reconstituted in the aprotic polar solvent, and the second dried peptide maintains the second pH memory when the second dried peptide is reconstituted in the aprotic polar solvent).

In the process for making stable peptide formulations, suitable non-volatile buffers include, for example, glycine buffers, citrate buffers, phosphate buffers, and mixtures thereof. In some embodiments, the non-volatile buffer is a glycine buffer or a citrate buffer. In some embodiments, the non-volatile buffer is a mixture of a citrate buffer and a phosphate buffer. In some embodiments, the peptide is mixed with both the non-volatile buffer and a stabilizing excipient (such as a sugar, a starch, or mixtures thereof) and then dried to a dried peptide powder. In other embodiments, the stabilizing excipient (such as a sugar, a starch, a sugar alcohol, or mixtures thereof) is added to the reconstituted peptide in the aprotic polar solvent. In some embodiments, the stabilizing excipient is present in the formulation in an amount ranging from about 1% (w/v) to about 60% (w/v), e.g., about 1%, about 5%, about 10%, about 15%, about 20%, about 25%, about 30%, about 35%, about 40%, about 45%, about 50%, about 55%, or about 60% (w/v). In some embodiments, the stabilizing excipient is trehalose. In some embodiments, the stabilizing excipient is HES. In some embodiments, the stabilizing excipient is a mixture of trehalose and HES.

As explained above, when the peptide is mixed with the non-volatile buffer, the non-volatile buffer is selected such that the peptide has a pH of maximal stability/minimal degradation in the aqueous environment. Once dried, the peptide will have a pH memory of maximal stability/minimal degradation and will retain that pH memory when dissolved in or reconstituted in the aprotic polar solvent. As such, in one embodiment, the pH of the non-volatile buffer is such that the dried peptide powder has a pH memory of about 2 to about 3. In another embodiment, the pH of the non-volatile buffer is such that the dried peptide powder has a pH memory of about 4 to about 6. In yet another embodiment, the pH of the non-volatile buffer is such that the dried peptide powder has a pH memory of about 4 to about 5. In yet another embodiment, the pH of the non-volatile buffer is such that the dried peptide powder has a pH memory of about 6 to about 8.

Once the peptide and the non-volatile buffer (and optionally other components, such as a stabilizing excipient, that are added to the peptide and the non-volatile buffer before drying) are dried to a powder, the dried peptide powder is dissolved or reconstituted in an aprotic polar solvent as described herein (e.g., dimethylsulfoxide (DMSO), n-methyl pyrrolidone (NMP), ethyl acetate, and mixtures thereof). In some embodiments, the aprotic polar solvent is dimethylsulfoxide (DMSO). In other embodiments, the aprotic polar solvent is n-methyl pyrrolidone (NMP).

In some embodiments, the step of reconstituting the dried peptide powder comprises diluting or reconstituting the dried peptide with a mixture comprising an aprotic polar solvent and a co-solvent that depresses the freezing point of the formulation. In some embodiments, the co-solvent is selected from ethanol, propylene glycol, glycerol, and mixtures thereof. In some embodiments, the co-solvent is present in the formulation in an amount ranging from about 10% (w/v) to about 50% (w/v), e.g., about 10%, about 15%, about 20%, about 25%, about 30%, about 35%, about 40%, about 45%, or about 50% (w/v).

The formulations of the present invention have very little residual moisture and, thus, the peptides in such formulations remain stable over extended periods of time. In preferred embodiments, the moisture content of the stable formulation that is made by the process of the present invention is less than 4%, less than 3%, less than 2%, less than 1%, less than 0.5%, less than 0.4%, less than 0.3%, less than 0.25%, less than 0.2%, less than 0.15%, less than 0.1%, less than 0.075%, less than 0.05%, less than 0.025%, or less than 0.01%.

In the foregoing process, drying of the peptide compound with the non-volatile buffer (and optionally the stabilizing excipient) is carried out using spray-drying techniques, freeze-drying techniques or lyophilization techniques. Spray-drying techniques are well known to those skilled in the art. Spray-drying includes the steps of atomization of a solution containing one or more solid (e.g., therapeutic agent) via a nozzle spinning disk, or other device, followed by evaporation of the solvent from the droplets. The nature of the powder that results is the function of several variables including the initial solute concentration, size distribution of droplets produced and the rate of solute removal. The particles produced may comprise aggregates of primary particles which consist of crystals and/or amorphous solids depending on the rate and conditions of solvent removal.

A spray-drying process for preparing ultra-fine powders of biological macromolecules such as proteins, oligopeptides, high molecular weight polysaccharides, and nucleic acids is described in, for example, U.S. Pat. No. 6,051,256. Freeze-drying procedures are well known in the art, and are described, for example, in U.S. Pat. No. 4,608,764 and U.S. Pat. No. 4,848,094. Spray-freeze-drying processes are described, e.g., in U.S. Pat. No. 5,208,998. Other spray-drying techniques are described, for example, in U.S. Pat. Nos. 6,253,463; 6,001,336; 5,260,306; and PCT International Publication Nos. WO 91/16882 and WO 96/09814.

Lyophilization techniques are well known to those skilled in the art. Lyophilization is a dehydration technique that takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products, and are described, e.g., in U.S. Pat. No. 6,199,297. "Standard" lyophilization conditions, are described, e.g., in U.S. Pat. No. 5,031,336, and in "Freeze Drying of Pharmaceuticals" (DeLuca, Patrick P., J. Vac. Sci. Technol., Vol. 14, No. 1, January/February 1977); and "The Lyophilization of Pharmaceuticals: A Literature Review" (Williams, N. A., and G. P. Polli, Journal of Parenteral Science and Technology, Vol. 38, No. 2, March/April 1984).

In certain preferred embodiments, the lyophilization cycle is partially performed above the glass transition temperature (Tg) of the therapeutic agent formulation to induce a collapse of the mass to form a dense cake containing residue moisture. In other embodiments, the lyophilization cycle is carried out below the glass transition temperature in order to avoid a collapse in order to achieve a complete drying of the particles.

V. Therapeutic Methods

In another aspect, the present invention provides methods of treating diseases or conditions by administering to a subject a stable formulation as described herein in an amount effective to treat, alleviate or prevent the disease, condition or disorder. In some embodiments, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia. In some embodiments, the disease, condition, or disorder is diabetes.

In some embodiments, a therapeutic method of the present invention comprises treating hypoglycemia by administering to a subject having hypoglycemia a stable formulation as described herein in an amount effective to treat the hypoglycemia. In some embodiments, the subject is administered a stable formulation comprising glucagon.

In some embodiments, a therapeutic method of the present invention comprises treating diabetes by administering to a subject having diabetes a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

Administered dosages for the peptide drugs as described herein for treating a disease, condition, disorder (e.g., a diabetic condition, e.g., hypoglycemia or diabetes) are in accordance with dosages and scheduling regimens practiced by those of skill in the art. General guidance for appropriate dosages of all pharmacological agents used in the present methods is provided in *Goodman and Gilman's The Pharmacological Basis of Therapeutics,* 11th Edition, 2006, supra, and in a Physicians' Desk Reference (PDR), for example, in the 65th (2011) or 66th (2012) Eds., PDR Network, LLC, each of which is hereby incorporated herein by reference. The appropriate dosage of a peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a peptide drug. The dosage can be increased or decreased over time, as required by an individual patient.

Determination of an effective amount or dose is well within the capability of those skilled in the art, especially in light of the detailed disclosure provided herein. Generally, the formulations to deliver these doses may contain one, two, three, four, or more peptides or peptide analogs (collectively "peptide," unless peptide analogs are expressly excluded), wherein each peptide is present at a concentration from about 0.1 mg/mL up to the solubility limit of the peptide in the formulation. This concentration is preferably from about 1 mg/mL to about 100 mg/mL, e.g., about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL.

The formulations of the present invention may be for subcutaneous, intradermal, or intramuscular administration (e.g., by injection or by infusion). In some embodiments, the formulation is administered subcutaneously.

The formulations of the present disclosure are administered by infusion or by injection using any suitable device. For example, a formulation of the present invention may be placed into a syringe, a pen injection device, an auto-injector device, or a pump device. In some embodiments, the injection device is a multi-dose injector pump device or a multi-dose auto-injector device. The formulation is presented in the device in such a fashion that the formulation is readily able to flow out of the needle upon actuation of an injection device, such as an auto-injector, in order to deliver the peptide drugs. Suitable pen/autoinjector devices include, but are not limited to, those pen/autoinjection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In another aspect, the present invention provides for the use of a stable formulation as described herein for the formulation of a medicament for the treatment of any disease, condition, or disorder that may be treated with the peptide of the formulation. In some embodiments, the stable formulation is used for formulating a medicament for the treatment of a diabetic condition, e.g., type 1 diabetes, type 2 diabetes, gestational diabetes, pre-diabetes, hyperglycemia, hypoglycemia, or metabolic syndrome.

In some embodiments, the stable formulation is used for formulating a medicament for the treatment of hypoglycemia. In some embodiments, the stable formulation comprises glucagon or a salt thereof (e.g., glucagon acetate). In some embodiments, the stable formulation comprises glucagon and exenatide.

In some embodiments, the stable formulation is used for formulating a medicament for the treatment of diabetes. In some embodiments, the stable formulation comprises insulin. In some embodiments, the stable formulation comprises exenatide. In some embodiments, the stable formulation comprises pramlintide. In some embodiments, the stable formulation comprises insulin and pramlintide.

VI. Kits

In another aspect, the present invention kits for treating a disease, condition or disorder as described herein. In some embodiments, the kit comprises: a stable formulation comprising one, two, three, four or more peptides or salts thereof, wherein the peptide(s) has been dried in a non-volatile buffer, and wherein the dried peptide(s) has a pH memory that is about equal to the pH of the peptide(s) in the non-volatile buffer; and an aprotic polar solvent; wherein the moisture content of the formulation is less than 5%, and wherein the dried peptide(s) maintains the pH memory that is about equal to the pH of the peptide(s) in the non-volatile buffer when the dried peptide(s) is reconstituted in the aprotic polar solvent; and a syringe for administration of the stable formulation to the subject.

In some embodiments, the kit comprises a stable glucagon formulation as described herein for use in treating hypoglycemia in a subject. In some embodiments, the kit comprises a glucagon formulation comprising: glucagon or a salt thereof (e.g., glucagon acetate), wherein the glucagon has been dried in a non-volatile buffer, and wherein the dried glucagon has a pH memory that is about equal to the pH of the glucagon in the non-volatile buffer selected from a glycine buffer, a citrate buffer, a phosphate buffer, and mixtures thereof, wherein the pH memory of the dried glucagon is from about 2.0 to about 3.0; and an aprotic polar solvent selected from dimethylsulfoxide (DMSO), n-methyl pyrrolidone (NMP), ethyl acetate, and mixtures thereof; wherein the moisture content of the formulation is less than 1%, and wherein the dried glucagon maintains the pH memory that is about equal to the pH of the glucagon in the non-volatile buffer when the dried glucagon is reconstituted in the aprotic polar solvent. In some embodiments, the glucagon formulation further comprises a co-solvent that depresses the freezing point of the formulation, wherein the co-solvent is selected from ethanol, propylene glycol, glycerol, and mixtures thereof. In some embodiments, the glucagon formulation further comprises a stabilizing excipient selected from sugars, starches, and mixtures thereof. In some embodiments, the glucagon is present in the formulation in an amount ranging from about 1 mg/mL to about 50 mg/mL.

In some embodiments, the kit comprises a stable insulin and pramlintide formulation as described herein for use in treating diabetes in a subject. In some embodiments, the kit comprises an insulin and pramlintide formulation comprising: insulin, wherein the insulin has been dried in a first non-volatile buffer selected from a glycine buffer, a citrate buffer, a phosphate buffer, and mixtures thereof, and wherein the dried insulin has a first pH memory that is about equal to the pH of the insulin in the first non-volatile buffer, wherein the first pH memory is from about 1.5 to about 2.5 or from about 6.0 to about 8.0; pramlintide, wherein the pramlintide has been dried in a second non-volatile buffer selected from a glycine buffer, a citrate buffer, a phosphate buffer, and mixtures thereof, and wherein the dried pramlintide has a second pH memory that is about equal to the pH of the pramlintide in the second non-volatile buffer, wherein the second pH memory is from about 3.0 to about 5.0 or from about 4.0 to about 6.0; and an aprotic polar solvent selected from dimethylsulfoxide (DMSO), n-methyl pyrrolidone (NMP), ethyl acetate, and mixtures thereof; wherein the moisture content of the formulation is less than 1%, wherein the dried insulin maintains the first pH memory that is about equal to the pH of the insulin in the first non-volatile buffer when the dried insulin is reconstituted in the aprotic polar solvent, and wherein the dried pramlintide maintains the second pH memory that is about equal to the pH of the pramlintide in the second non-volatile buffer when the dried pramlintide is reconstituted in the aprotic polar solvent. In some embodiments, the insulin and pramlintide formulation further comprises a co-solvent that depresses the freezing point of the formulation, wherein the co-solvent is selected from ethanol, propylene glycol, glycerol, and mixtures thereof. In some embodiments, one or both of the insulin in the first non-volatile buffer and the pramlintide in the second non-volatile buffer further comprises a stabilizing excipient selected from sugars, starches, and mixtures thereof. In some embodiments, the first non-volatile buffer and the second non-volatile buffer are the same. In some embodiments, the first non-volatile buffer and the second non-volatile buffer are different. In some embodiments, each of the insulin and pramlintide is present in the formulation in an amount ranging from about 1 mg/mL to about 50 mg/mL. In some embodiments, the first pH memory is from about 1.5 to about 2.5. In some embodiments, the first pH memory is from about 6.0 to about 8.0. In some embodiments, the second pH memory is from about 3.0 to about 5.0. In some embodiments, the second pH memory is from about 4.0 to about 6.0. In some embodiments, the first pH memory is from about 1.5 to about 2.5 and the second pH memory is from about 3.0 to about 5.0.

In some embodiments, the kit comprises a syringe that is part of a pen injection device, an auto-injector device or a pump. In some embodiment, the syringe is prefilled with the stable formulation. In some embodiments, the kit further comprises instructions, wherein the instructions direct the administration of the stable formulation to treat the subject in need thereof (e.g., the subject having hypoglycemia or diabetes).

VII. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Preparation of Glucagon Solutions for Use in Freeze-Drying

Various solutions were prepared to contain glucagon at a concentration of 10 mg/mL. The solutions contained, alternatively, glycine, citrate or phosphate at 5 mM, generally providing a buffer establishing a pH of 3. The solution also contained a sugar, alone or in combination, in amounts equal to the w/v amount of glucagon (1:1) or at 200% (2:1) of the amount of glucagon. The sugars were trehalose, HES, and β-cyclodextrin (β-CD). Some solutions also contained Tween-20 at 0.10% w/v as a surfactant. The various formulations were mixed to substantial homogeneity in amounts as described in Table 1 below.

TABLE 1

Glucagon Mixtures for Subsequent Lyophilization

| Formulation # | Glucagon (mg/ml) | Glycine Buffer (mM) | Citrate Buffer (mM) | Phosphate Buffer (mM) | Trehalose (mg/ml) | HES (mg/ml) | β-CD (mg/ml) | Tween-20 (mg/ml) |
|---|---|---|---|---|---|---|---|---|
| 1 | 5 | 5 | 0 | 0 | 0 | 0 | 0 | 0 |
| 2 | 5 | 5 | 0 | 0 | 0 | 0 | 0 | 0.01 |
| 3 | 5 | 5 | 0 | 0 | 10 | 0 | 0 | 0 |
| 4 | 5 | 5 | 0 | 0 | 0 | 10 | 0 | 0 |
| 5 | 5 | 5 | 0 | 0 | 5 | 5 | 0 | 0 |
| 6 | 5 | 5 | 0 | 0 | 0 | 0 | 10 | 0 |
| 7 | 5 | 0 | 5 | 0 | 0 | 0 | 0 | 0 |
| 8 | 5 | 0 | 5 | 0 | 0 | 0 | 0 | 0.01 |
| 9 | 5 | 0 | 5 | 0 | 10 | 0 | 0 | 0 |
| 10 | 5 | 0 | 5 | 0 | 0 | 10 | 0 | 0 |
| 11 | 5 | 0 | 5 | 0 | 5 | 5 | 0 | 0 |
| 12 | 5 | 0 | 5 | 0 | 0 | 0 | 10 | 0 |
| 13 | 5 | 0 | 0 | 5 | 0 | 0 | 0 | 0 |
| 14 | 5 | 0 | 0 | 5 | 0 | 0 | 0 | 0.01 |
| 15 | 5 | 0 | 0 | 5 | 10 | 0 | 0 | 0 |
| 16 | 5 | 0 | 0 | 5 | 0 | 10 | 0 | 0 |
| 17 | 5 | 0 | 0 | 5 | 5 | 5 | 0 | 0 |
| 18 | 5 | 0 | 0 | 5 | 0 | 0 | 10 | 0 |
| 19 | 5 | 5 | 0 | 0 | 10 | 0 | 0 | 0.01 |
| 20 | 5 | 5 | 0 | 0 | 0 | 10 | 0 | 0.01 |
| 21 | 5 | 5 | 0 | 0 | 5 | 5 | 0 | 0.01 |

To prepare the mixtures, the glucagon was dissolved in the respective buffers (phosphate, citrate, and/or glycine buffers, 5 mM, pH 3.0) at 10 mg/mL. The solution was then mixed in a 1:1 (v/v) ratio with various solutes, which were prepared at twice the desired concentration using corresponding buffer, in order to obtain a final glucagon concentration of 5 mg/mL and the final desired solute concentration. The solutions were then filtered through 0.2 μm Millipore PES membrane to remove insoluble materials. The sample preparations were conducted in a 4° C. cold room. The glucagon concentration and the purity were determined by RP- and Size-Exclusion (SE)-HPLC.

Example 2

Preparation of Dry Glucagon Powder by Freeze-Drying

The above formulations of Table 1 were pipetted (0.3 mL) into 3-mL lyophilization vials (13-mm ID). The formulations were lyophilized in a FTS Durastop freeze-drier (Stoneridge, N.Y.). Samples were frozen at −40° C. at a ramp of 2.5° C./min and maintained for 2 hours (h) to allow sufficient freezing. The sample temperature was then increased to −5° C. at a ramp of 2° C./min and held for 2 h as an annealing step. The temperature was then decreased to 30° C. at a ramp of 1.5° C./min and the vacuum was turned on at 60 mTorr. The primary drying was set for 24 h. The temperature was gradually increased to 40° C. at a ramp of 0.5° C./min and held for additional 10 h. After drying was complete, the vials were capped under vacuum using XX stoppers from the West Pharmaceutical company (product #10123524). None of the formulations showed any evidence of cake collapse following freeze-drying. The moisture content of the final dried product was less than 1% w/w.

Example 3

Preparation of Glucagon Formulations in Aprotic Polar Solvents

Six of the dry powders made from the solutions in Table 1 were selected for formulation in polar, aprotic solvents:

1. Buffer (glycine)+trehalose (200% relative to glucagon) (formulation #3)
2. Buffer (glycine)+HES (200% relative to glucagon) (formulation #4)
3. Buffer (glycine)+trehalose (100% relative to glucagon)+ HES (100% relative to glucagon) (formulation #5)
4. Buffer (glycine)+Tween-20 (0.01% w/v)+trehalose (200% relative to glucagon) (formulation #19)
5. Buffer (glycine)+Tween-20 (0.01% w/v)+HES (200% relative to glucagon) (formulation #20)
6. Buffer (glycine)+Tween-20 (0.01% w/v)+trehalose (100% relative to glucagon)+HES (100% relative to glucagon) (formulation #21)

Example 4

Preparation of a Glucagon Solution with a pH Memory of 4-5

Solutions were prepared to contain glucagon at a concentration of 10-20 mg/mL. The solutions contained a citrate buffer establishing pH of 4-5. The solution also contained a sugar alcohol, mannitol, at a concentration of 50-100 mg/mL. The formulation was mixed to substantial homogeneity and freeze-dried via the drying cycle described in Example 2 to a residual moisture of less than 0.5% w/w. The dry powder is dissolved into DMSO to a concentration of 10-20 mg/mL of glucagon and 50-100 mg/mL of mannitol.

Example 5

Preparation of a PTH(1-34) Solution with Low Moisture and Low Freezing Point

Solutions were prepared to contain PTH (1-34) at a concentration of 10-20 mg/mL. The solutions contained a citrate buffer establishing pH of 4-5. The solution also contained a sugar alcohol, mannitol, at a concentration of 50 mg/mL. The formulation was mixed to substantial homogeneity and freeze-dried via the drying cycle described in Example 2 to a residual moisture of less than 0.5% w/w. The dry powder is dissolved into DMSO to a concentration of 10-20 mg/mL of PTH (1-34) and 50-100 mg/mL of mannitol.

Example 6

Increase in Both Blood Glucagon and Blood Glucose Levels Following Administration of Glucagon Formulation Two nonaqueous glucagon formulations in aprotic polar solvents, based on glucagon-glycine-trehalose powders dissolved in NMP or DMSO, were tested in a rat pharmacokinetic and pharmacodynamic study and compared with an aqueous formulation. Rats were all dosed at a rate of 10 μg glucagon/rat. The nonaqueous glucagon solutions were given as 10 μL subcutaneous injections, as was the aqueous control solution. All formulations tested demonstrated a rapid rise in blood glucagon concentrations (see FIG. 1).

Pharmacokinetic (PK) parameters were analyzed for the four treatment groups plus the aqueous control. A noncompartmental PK analysis was performed for each rat. $C_{max}$ and $T_{max}$ were computed from observed data. Area-under-the-curve (AUC) estimates were computed without extrapolation. Data were analyzed using a five group ANOVA to compare PK parameters across groups. No significant differences in either $C_{max}$, $T_{max}$ or AUC among the three groups was observed. The relative bioavailabilities of the NMP and DMSO formulations relative to the aqueous control group were all close to 100% (76% and 92%, respectively). Thus, the nonaqueous formulations are essentially bioequivalent to the aqueous glucagon formulation based on the results of these rat PK studies.

Figure 2:
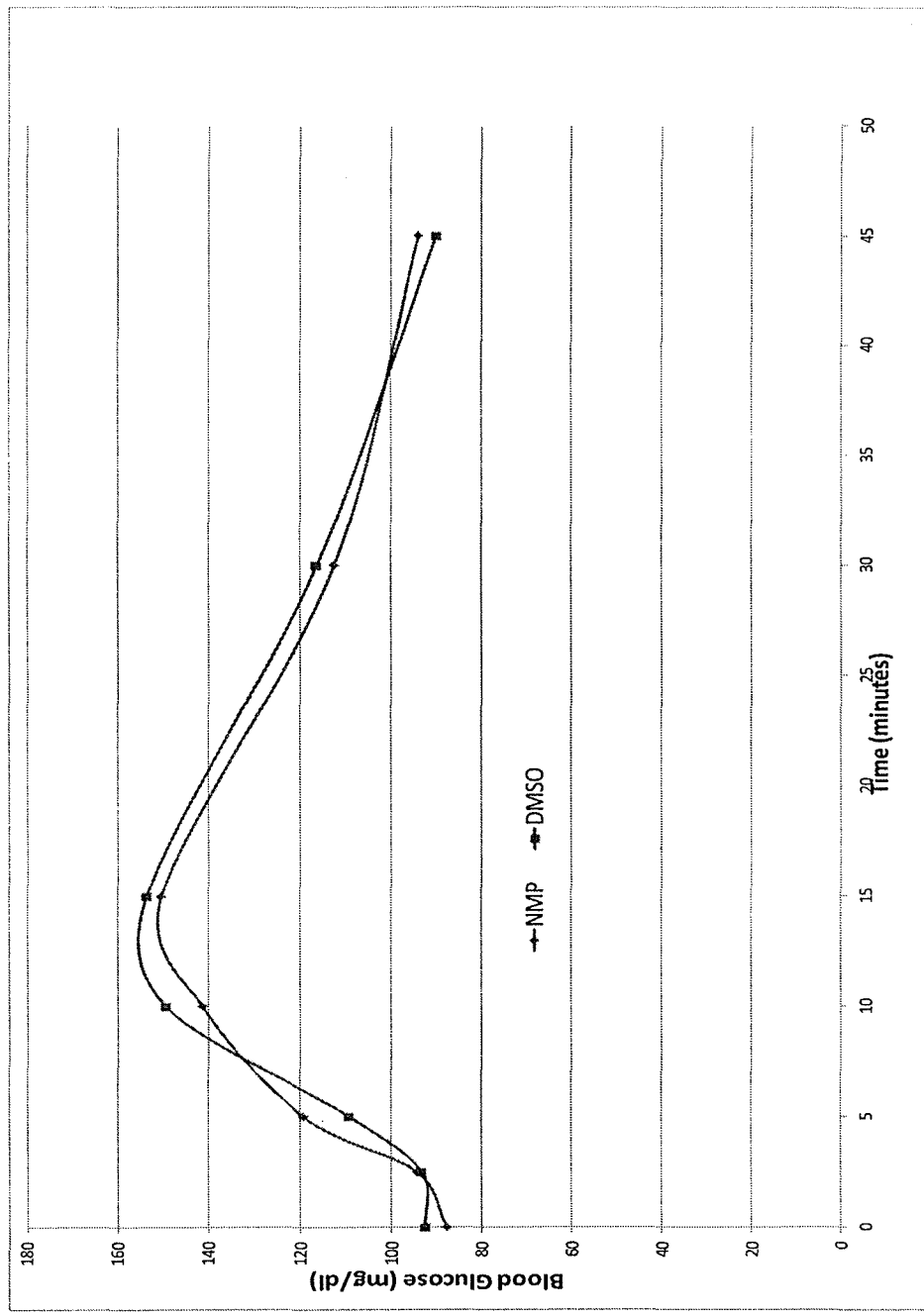
FIG. 2 illustrates blood glucose levels after injection of freeze-dried glucagon-glycine-trehalose dissolved in DMSO or NMP.

As predicted from the pharmacokinetic results, the nonaqueous glucagon formulations produced pharmacodynamic profiles essentially equivalent to an aqueous-reconstituted glucagon formulation at the same dose level (see, FIG. 2).

Example 7

Enhanced Solubility of Glucagon in Aprotic Polar Solvents Compared to Aqueous Solutions Glucagon was prepared at 1.0 mg/mL via dissolution in one of the following buffers:
1. 2 mM citric acid, pH 2.0 (titrated with concentrated HCl) ("C2.0")
2. 2 mM citric acid, pH 3.0 (titrated with concentrated HCl) ("C3.0")

Each formulation was placed in sterile 2 cc vials, at 1 mL fill volume. Samples were freeze-dried to low residual moisture and reconstituted to various nominal concentrations in DMSO, NMP, or a 50/50 DMSO/NMP co-solvent. Reconstitution concentrations ranged from 1 to 30 mg/mL. Solubility was measured by visual inspection for clarity, turbidity via $A_{630}$, and RP-HPLC.

As shown in Table 2 below, glucagon lyophilized with a citrate buffer at pH memories of 2.0 and 3.0 were readily soluble to concentrations of 30 mg/mL. The same formulations were only fully soluble in $H_2O$ at lower concentrations. For pH memory of 3.0, complete reconstitution was only achieved at 5 mg/mL in $H_2O$. Further, glucagon solubilized in $H_2O$ was only meta-stable, i.e., it only remained soluble for a few hours and then began to gel or fibrillate with rates dependent on pH and concentration, whereas glucagon solubilized in the aprotic polar solvents/co-solvents were stable indefinitely.

TABLE 2

Solubility of glucagon at pH memory of 2.0 and 3.0

| Formulation | Solvent | 1 mg/ml | 5 mg/ml | 10 mg/ml | 20 mg/ml | 30 mg/ml |
|---|---|---|---|---|---|---|
| C2.0 | H₂0 | 1 | 5 | 10 | 18 | 24 |
|  | DMSO | 1 | 5 | 10 | 20 | 30 |
|  | DMSO/NMP | 1 | 5 | 10 | 20 | 30 |
|  | NMP | 1 | 5 | 10 | 20 | 30 |
| C3.0 | H₂0 | 1 | 5 | 7 | 17 | 9 |
|  | DMSO | 1 | 5 | 10 | 20 | 30 |
|  | DMSO/NMP | 1 | 5 | 10 | 20 | 30 |
|  | NMP | 1 | 5 | 10 | 20 | 30 |

Example 8

Effect of pH on the Solubility of Glucagon in Aprotic Polar Solvents

When the data shown in Example 8 and Table 2 is viewed from a pH memory perspective, it is apparent that higher solubilities for glucagon can be achieved in the aprotic polar solvents at a lower pH memory (e.g., pH 2.0) than at a higher pH. Furthermore, although the recoveries in Table 2 indicate essentially 100% of the nominal concentration, $A_{630}$ measurements showed increasing turbidity of 30 mg/mL solutions of glucagon at pH memory of 3.0 (C3.0) in neat NMP and the DMSO/NMP co-solvent, whereas the C2.0 formulations with a pH memory of 2.0 remained essentially free of turbidity.

In another example, the effect of pH on the solubility of glucagon in aprotic polar solvents was measured for glucagon acetate dissolved in $H_2O$ at 2 mg/mL with either 2 mL glycine or 2 mM citrate buffer and pH adjusted to the desired value. Samples were freeze-dried and reconstituted to various nominal concentrations in DMSO, NMP, or a 50/50 DMSO/NMP co-solvent. Solubility was measured by visual inspection for clarity, turbidity via $A_{630}$, and RP-HPLC.

It was found that "pH memory" from lyophilization had a major effect on glucagon stability. Glucagon was soluble at up to 30 mg/mL reconstitution for "G2.5" (pH memory 2.5) lyophiles DMSO, DMSO/NMP, and NMP. Significantly reduced solubility was observed for "G3.5" (pH memory 3.5) lyophiles. G3.5 lyophiles all were cloudy and recoveries were less than complete, even at a nominal reconstitution concentration of 10 mg/mL. DMSO and the DMSO/NMP co-solvent showed about 95% recovery, whereas NMP showed only about 60% recovery.

Example 9

Effect of Buffer Species on Glucagon Stability in DMSO

Glucagon acetate was prepared at 1.0 mg/mL via dissolution in one of the following buffers:
1. 2 mM L-glycine, pH 3.0 (titrated with concentrated HCl)
2. 2 mM citric acid, pH 3.0 (titrated with concentrated HCl)

These formulations were lyophilized and reconstituted in DMSO at a nominal concentration of 5 mg/mL glucagon. Formulations were placed in stability incubators at 5° C., 25° C., and 40° C. Glucagon purity was determined with a reverse phase HPLC method.

The stability of the formulation in glycine buffer was significantly greater after 1 month of incubation at the various temperatures. Table 3 below shows the RP-HPLC purity at various times of incubation at 40° C.

TABLE 3

Effect of buffer species on the stability of glucagon in DMSO

| Formulation | Time = 0 | 1 week | 2 weeks | 4 weeks |
|---|---|---|---|---|
| Glycine, pH 3.0 | 99.4 | 99.1 | 99.0 | 96.6 |
| Citrate, pH 3.0 | 98.6 | 97.7 | 97.3 | 92.7 |

Example 10

Effect of Moisture on Glucagon Stability in DMSO

Glucagon acetate was prepared at 1.0 mg/mL via dissolution in one of the following buffers:
1. 2 mM L-glycine, pH 3.0 (titrated with concentrated HCl)
2. 2 mM L-glycine, pH 3.0 (titrated with concentrated HCl)

These formulations were lyophilized and reconstituted in DMSO at a nominal concentration of 5 mg/mL glucagon. Additional moisture was added to the second formulation. Moisture content was measured using the Karl Fisher method. The first formulation had a moisture content of 0.13% (w/w), whereas the second formulation had a moisture content of 0.54% (w/w). Formulations were placed in stability incubators at 5° C., 25° C., and 40° C. Glucagon purity was determined with a reverse phase HPLC method.

The stability of the formulation with lower moisture was significantly greater after 1 month of incubation at the various temperatures. Table 4 below shows the RP-HPLC purity at various times of incubation at 40° C. Even at moisture contents below 1%, a significant difference in stability can be detected.

TABLE 4

Effect of residual moisture on the stability of glucagon in DMSO

| Formulation | Time = 0 | 1 week | 2 weeks | 4 weeks |
|---|---|---|---|---|
| Lower moisture | 99.4 | 99.1 | 99.0 | 96.6 |
| Additional moisture | 99.2 | 98.9 | 98.8 | 95.6 |

Example 11

Freezing Point Depression of DMSO Solutions

Using PerkinElmer Instruments PYRIS Diamond Differential Scanning Calorimetry ("DSC"), samples were cooled to −40° C. and heated to 40° C. at 8° C. per minute for screening purposes.
DMSO/NMP Blends
Various DMSO and NMP blends were tested, including:
1. 90% DMSO+10% NMP
2. 80% DMSO+20% NMP
3. 70% DMSO+30% NMP
4. 60% DMSO+40% NMP
5. 50% DMSO+50% NMP DSC scans showed that the temperature of crystallization of the solvents progressively reduced from =18° C. for neat DMSO to −5.7° C. for a 50% NMP/50% DMSO blend. Addition of the glucagon acetate, glycine lyophile to a glucagon concentration of 5 mg/mL resulted in an additional ~1° C. reduction in the freezing point.

DMSO/Ethyl Acetate Blends
Various DMSO and ethyl acetate blends were tested, including:
1. 80% DMSO+20% ethyl acetate ($T_c$=16° C.)
2. 70% DMSO+30% ethyl acetate
3. 60% DMSO+40% ethyl acetate ($T_c$=6.5° C.)
4. 50% DMSO+50% ethyl acetate ($T_c$=2.9° C.)
5. 40% DMSO+60% ethyl acetate ($T_e$=none observed)

DSC scans showed that the temperature of crystallization of the solvents progressively reduced from ~18° C. for neat DMSO to 2.9° C. for a 50% NMP/50% DMSO blend. No crystallization peak was observed for a 40% DMSO/60% ethyl acetate blend. Additionally, these formulations were stored at refrigerated temperature (4° C.) for several days and observed visually for evidence of freezing. All formulations with 30% ethyl acetate or greater in the co-solvent stayed liquid and did not freeze. This is somewhat different from the $T_c$ observed in the DSC studies.

DMSO Solutions with Alcohol Co-Solvents
Various DMSO solutions to which an alcohol co-solvent (ethanol, glycerol, or propylene glycol) were added were tested, including:
1. 95% DMSO+5% alcohol
2. 90% DMSO+10% alcohol
3. 80% DMSO+20% alcohol
4. 70% DMSO+30% alcohol
5. 60% DMSO+40% alcohol
6. 50% DMSO+50% alcohol
7. 40% DMSO+60% alcohol
8. 30% DMSO+70% alcohol
9. 20% DMSO+80% alcohol
10. 10% DMSO+90% alcohol These formulations were stored at refrigerated temperature (4° C.) for several days and observed visually for evidence of freezing. All formulations with 20% alcohol co-solvent or greater stayed liquid and did not freeze. DSC scans showed the freezing point of 20% alcohol co-solvents to be 2.3° C., 0.6° C., and 3.3° C. for ethanol, glycerol, and propylene glycol, respectively.

Example 12

Freeze-Thaw Stability of Glucagon

Glucagon acetate was prepared at 1.0 mg/mL via dissolution in 2 mM L-glycine, pH 3.0 (titrated with concentrated HCl). The glucagon formulations were lyophilized and reconstituted in DMSO at a nominal concentration of 5 mg/mL glucagon. Solution samples were divided and trehalose was added to one solution to a concentration of 5%. These formulations were aliquoted into vials and placed in a stability incubator at 5° C. At 5° C., these solutions were observed to freeze. The glucagon solutions were thawed at various interals and turbidity was determined using the absorbance at 630 nm.

Table 5 below shows the turbidity of the glucagon solutions at various times of incubation at 5° C. The solutions without trehalose showed increases in turbidity at various timepoints of incubation. Solutions containing trehalose, however, showed no increase in turbidity. The turbidity measurements were confirmed through visual observation. Samples frozen and incubated without trehalose were cloudy or hazy upon observation.

TABLE 5

Turbidity of glucagon solutions after incubation at 5° C.

| Formulation | Time = 0 | 1 week | 2 weeks | 4 weeks |
|---|---|---|---|---|
| No trehalose | 0.024 | 0.142 | 0.130 | 0.160 |
| 5% trehalose | 0.016 | 0.029 | 0.028 | 0.035 |

Surprisingly, use of a carbohydrate additive such as trehalose in solutions of peptides in DMSO enhances the stability of the peptide during the freeze-thawing process.

Example 13

Enhanced Thawing Rate with Trehalose

Glucagon acetate was prepared at 1.0 mg/mL via dissolution in 2 mM L-glycine, pH 3.0 (titrated with concentrated HCl) as described above for Example 13. Upon removal from storage at 5° C., samples of glucagon solutions containing trehalose were observed to thaw completely in a much shorter time than solutions without trehalose. Trehalose-containing samples were observed to thaw completely in less than 30 seconds, as contrasted with glucagon solutions without trehalose, which were typically observed to thaw completely over several minutes. The ability to quickly thaw a peptide formulation can be particularly advantageous in an emergency medical setting, in the event a solution was frozen and had to be injected rapidly.

Example 14

Effect of pH on Insulin Solubility

Insulin was dissolved in $H_2O$ at 10 mg/mL with a 10 mM phosphate/citrate-1 mM EDTA buffer at either pH 2 or pH 7. These solutions were lyophilized to dryness (>1% residual moisture) using a conservative cycle and reconstituted to various nominal concentrations in DMSO. Solubility was measured by visual inspection for clarity and turbidity via $A_{630}$.

At a pH of 2, insulin was observed to be soluble to concentrations of at least 100 mg/mL. However, at a pH memory of 7, even at the lowest concentration tested, 10 mg/mL, poor solubility of insulin was observed as cloudy or hazy solutions with increased light scattering ($A_{630}$). Some lower-concentration, e.g., 10 mg/mL, insulin solutions with a pH memory of 7 were observed to slowly dissolve to a clear solution over a period of about 24 hours.

Example 15

Effect of pH on Pramlintide Solubility

Pramlintide acetate was dissolved in $H_2O$ at 2 mg/mL with either a 10 mM citrate buffer, pH 4 or 10 mM phosphate buffer, pH 7. These solutions were lyophilized to dryness (>1% residual moisture) using a conservative cycle and reconstituted to various nominal concentrations in DMSO. Solubility was measured by visual inspection for clarity and turbidity via $A_{630}$.

At no concentration was pramlitide with a pH memory of 7 soluble in DMSO. However, a low concentration of pramlintide with a pH memory of 4 was soluble in DMSO.

Example 16

Co-Formulations of Peptides in Aprotic Polar Solvents

Preparation of co-formulations are prepared by separately drying formulations of the individual compounds from an aqueous solution that provides the optimal solubility/stability upon reconstitution into the aprotic polar solvent. Solution pH is a property that affects peptide solubility, and a dried peptide, when reconstituted into an aprotic polar solvent, will retain a "pH memory" of the aqueous formulation from which it was dried when a non-volatile buffer is used. Since aprotic polar solvents do not have exchangeable protons, the individual peptides will maintain the solubility and stability characteristics of the optimal pH memory.

Current pramlintide and insulin formulations conflict in their buffering systems, making compatibility of a mixed formulation difficult. Most insulins and insulin analogs have an isoelectric point in the range of 5-6 and are thus formulated at a pH of around 7 or at a lower pH of around 2. Pramlintide has an isoelectric point of >10.5 and is formulated at a pH of around 4 where it is optimally stable. The interaction of pramlintide and insulin formulations at different pHs and differing buffering capacities often results in precipitation of soluble insulin components or solubilization of crystalline insulin components. In vitro studies with pramlintide and short- and long-acting insulin formulations found substantial variability in insulin solubility when various quantities of insulin were mixed with fixed quantities of pramlintide.

Thus, the present invention provides a formulation whereby both a rapid-acting insulin species and an amylin analog are stable and can be administered simultaneously from a single formulation for injection or formulation. This formulation more closely mimics the natural physiological response to post-prandial rise in blood glucose than the prior art.

Examples of peptides that can be co-formulated include, but are not limited to: (1) insulin-amylin (insulin at a pH memory of about 2.0 or about 7.0, and amylin or an amylin analog (e.g., pramlintide) at a pH memory of about 4.0); and (2) glucagon-GLP-1 (glucagon at a pH memory of about 3.0 or below, and glucagon-like peptide-1 (GLP-1) or an analog thereof (e.g., exenatide) at a pH memory of about 4.0-5.0).

A co-formulation of insulin and pramlintide was prepared as follows: An insulin formulation of 100 mg/mL insulin, pH memory 2, was made as described above in Example 14. A pramlintide formulation of 1 mg/mL pramlintide, pH memory 4, was made as described above in Example 15. 5 µl of the insulin formulation was mixed with 95 ml of the pramlintide solution. The resulting solution was observed to be clear and thus created a soluble co-formulation of insulin and pramlinitide with respective pH memory of 2 and 4, respectively.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents and PCT publications are incorporated herein by reference for all purposes.

What is claimed is:

1. A method comprising administering a stable solution to a subject, the stable solution comprising:

(a) a glucagon peptide or a salt thereof that has been dried from a non-volatile buffer; and
(b) an aprotic polar solvent;
wherein the glucagon peptide or salt thereof is reconstituted and solubilized in the aprotic polar solvent in an amount from about 0.1 mg/mL up to the solubility limit of the glucagon peptide or salt thereof, and the glucagon peptide or salt thereof has a pH memory in the aprotic polar solvent.

2. The method of claim 1, wherein the stable solution is administered with a syringe.

3. The method of claim 1, wherein the stable solution is administered with a pen injection device.

4. The method of claim 1, wherein the stable solution is administered with an auto-injector device.

5. The method of claim 1, wherein the stable solution is administered with a pump device.

6. The method of claim 1, wherein the non-volatile buffer is selected from a glycine buffer, a citrate buffer, a phosphate buffer, or mixtures thereof.

7. The method of claim 6, wherein the non-volatile buffer is a glycine buffer.

8. The method of claim 1, wherein the pH memory is about equal to the pH of the glucagon or salt thereof in the non-volatile buffer.

9. The method of claim 1, wherein the pH memory of the glucagon or salt thereof is from about 2 to 3.

10. The method of claim 1, wherein the pH memory of the glucagon or salt thereof is from 1 to 4.

11. The method of claim 1, wherein the aprotic polar solvent is selected from dimethylsulfoxide (DMSO), n-methyl pyrrolidone (NMP), ethyl acetate, and mixtures thereof.

12. The method of claim 11, wherein the aprotic polar solvent is n-methyl pyrrolidone (NMP).

13. The method of claim 12, wherein the aprotic polar solvent is dimethylsulfoxide (DMSO).

14. The method of claim 1, wherein the stable solution further comprises a co-solvent that depresses the freezing point of the formulation, wherein the co-solvent is selected from ethanol, propylene glycol, glycerol, and mixtures thereof.

15. The method of claim 1, wherein the stable solution further comprises a stabilizing excipient selected from a sugar, a starch, and mixtures thereof.

16. The method of claim 1, wherein the stable solution comprises from about 0.1 mg/mL to about 30 mg/mL of the glucagon or salt thereof.

17. The method of claim 1, wherein the buffer is a glycine buffer and the aprotic solvent is dimethylsulfoxide (DMSO).

18. The method of claim 17, wherein the stable solution further comprises a stabilizing excipient selected from sugars, starches, and mixtures thereof.

19. The method of claim 18, wherein the stabilizing excipient is trehalose.

20. The method of claim 1, wherein the water content of the stable solution is less than 5%.

21. The method of claim 1, wherein the stable solution further comprises a second peptide or salt thereof.

22. The method of claim 21, wherein the second peptide is a glucagon-like peptide-1 (GLP-1).

23. The method of claim 1, wherein the stable solution is administered parenterally.

24. The method of claim 1, wherein the stable solution is administered into an intradermal region of the subject.

25. The method of claim 1, wherein the stable solution is administered into a subcutaneous region of the subject.

26. The method of claim 1, wherein the stable solution is administered into an intramuscular region of the subject.

27. The method of claim 1, wherein the subject is a human.

\* \* \* \* \*